(12) United States Patent
De et al.

(10) Patent No.: US 12,065,407 B2
(45) Date of Patent: Aug. 20, 2024

(54) DUAL ACTING FKBP12 AND FKBP52 INHIBITORS

(71) Applicant: PLEX PHARMACEUTICALS, INC., San Diego, CA (US)

(72) Inventors: Surya Kanta De, San Diego, CA (US); Sridhar G. Prasad, San Diego, CA (US); Marshall C. Peterman, Oceanside, CA (US)

(73) Assignee: PLEX PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 16/640,919

(22) PCT Filed: Aug. 21, 2018

(86) PCT No.: PCT/US2018/047274
§ 371 (c)(1),
(2) Date: Feb. 21, 2020

(87) PCT Pub. No.: WO2019/040463
PCT Pub. Date: Feb. 28, 2019

(65) Prior Publication Data
US 2020/0399219 A1 Dec. 24, 2020

Related U.S. Application Data

(60) Provisional application No. 62/547,976, filed on Aug. 21, 2017, provisional application No. 62/547,977, filed on Aug. 21, 2017.

(51) Int. Cl.
| | |
|---|---|
| *C07D 213/30* | (2006.01) |
| *A61K 31/4184* | (2006.01) |
| *A61K 47/30* | (2006.01) |
| *C07C 237/22* | (2006.01) |
| *C07D 209/42* | (2006.01) |
| *C07D 231/56* | (2006.01) |
| *C07D 235/08* | (2006.01) |
| *C07D 235/10* | (2006.01) |
| *C07D 235/14* | (2006.01) |
| *C07D 235/30* | (2006.01) |
| *A61K 9/00* | (2006.01) |

(52) U.S. Cl.
CPC ............ *C07D 213/30* (2013.01); *A61K 47/30* (2013.01); *C07C 237/22* (2013.01); *C07D 209/42* (2013.01); *C07D 231/56* (2013.01); *C07D 235/10* (2013.01); *C07D 235/14* (2013.01); *C07D 235/30* (2013.01); *A61K 9/0043* (2013.01)

(58) Field of Classification Search
CPC .. C07D 235/08; C07D 235/10; C07D 235/14; A61K 31/4184
See application file for complete search history.

(56) References Cited

U.S. PATENT DOCUMENTS

| | | | |
|---|---|---|---|
| 3,707,559 A | 12/1972 | Mazur et al. | |
| 2003/0065007 A1 | 4/2003 | Creswell et al. | |
| 2009/0111874 A1 | 4/2009 | Nebolsin et al. | |
| 2009/0281129 A1* | 11/2009 | Chang ................ | G01N 33/5011 514/266.4 |
| 2014/0031363 A1 | 1/2014 | Liotta et al. | |

FOREIGN PATENT DOCUMENTS

| | | | |
|---|---|---|---|
| CN | 102688250 | * | 10/2012 |
| JP | 2009506086 A | | 2/2009 |
| WO | WO 2010111711 | * | 9/2010 |
| WO | 2016101885 A1 | | 6/2016 |
| WO | 2017017116 A1 | | 2/2017 |

OTHER PUBLICATIONS

Sullivan. Journal of Medicinal Chemistry, 1970, 13(4), 784-786 (Year: 1970).*
Tewari. Indian Journal of Chemistry, 2006, 45B, 489-493 (Year: 2006).*
Ascherio. The Lancet: Neurology, 2016, 15, 1257-1272 (Year: 2016).*
Lee. Journal of Neurochemistry, 2015, 133, 53-65, supporting information pp. S1-S17 (Year: 2015).*
Mak. ACS Chemical Biology, 2012, 7(7), 1190-1197, supplementary table 1 (Year: 2012).*
Sanguinet. Journal of Physical Chemistry B, 2006, 110, 10672-10682 (Year: 2006).*
Chen. Guangdong Huagong, 2009, 36(5), 18-20, 232, STN record thereof. (Year: 2009).*

(Continued)

*Primary Examiner* — Noble E Jarrell
(74) *Attorney, Agent, or Firm* — ArentFox Schiff LLP

(57) ABSTRACT

Provided are novel compounds of Formulas (I) and (II), pharmaceutically acceptable salts thereof, and pharmaceutical compositions thereof, which are useful as dual FKBP12/FKABP inhibitors. Also provided are pharmaceutical compositions comprising the novel compounds of Formulas (I) and (II) and their use in treating Parkinson's disease.

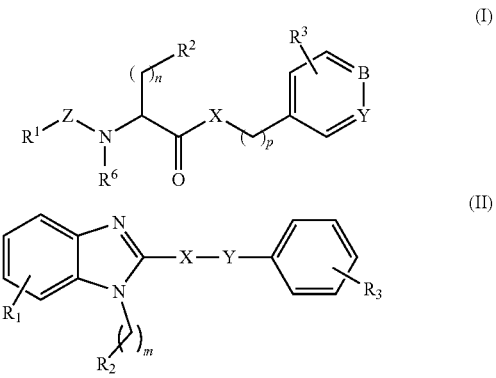

9 Claims, 6 Drawing Sheets

(56) References Cited

OTHER PUBLICATIONS

Tkachev. Zhurnal prikladnoi spektroskopii, 1965, 2(1), 63-68. (Year: 1965).*
Kolodyazhnaya. Khimiya Geterosiklichesskikh Soedineii, 1975, 6, 829-833, STN record thereof (Year: 1975).*
Le. Izvestiya Severo-Kavkazskogo Nauchnogo Tsentra Vysshei Shkoly Estestvennye Nauki, 1977, 5(1), 55-58. (Year: 1977).*
Shegal. Izvestiilja vysshikh uchebnykh zavedeniil, 1978, 21(9), 1258-1261. (Year: 1978).*
Kolodyazhnaya. Khimiya Geterotsiklicheskikh Soedinenii, 1990, 5, 637-642. (Year: 1990).*
Kolodyazhnaya. Khimiya Geterotsiklicheskikh Soedinenii, 1991, 9, 1209-1214 (Year: 1991).*
Kolodyazhnaya. Khimiya Geterotsiklicheskikh Soedinenii, 1983, (5), 661-666, STN record thereof. (Year: 1983).*
Laroche. Journal of Medicinal Chemistry, 2011, 54, 5059-5069 (Year: 2011).*
Ajani. International Research Journal of Pure and Applied Chemistry, 2013, 3(1), 10-21 (Year: 2013).*
Kumar, Asian Journal of Chemistry, 2013, 25 (17), 9569-9572 (Year: 2013).*
International Search Report and Written Opinion for PCT/US2018/047274 mailed Dec. 6, 2018.
J.T. Goodwin et al., "Physicochemical determinants of passive membrane permeability: role of solute hydrogen-bonding potential and volume", Journal of Medicinal Chemistry, vol. 44, No. 22, Sep. 25, 2001, pp. 3721-3729.
C.A. Olsen et al., "Side-chain-anchored N[alpha]-Fmoc-Tyr-OPfp for bidirectional solid-phase synthesis", Organic Letters, vol. 7, No. 9, Apr. 1, 2005 (Apr. 1, 2005), pp. 1703-1706.

V.M. Balaramnavar et al. "Identification of novel 2-((1-(benzyl (2-hydroxy-2-phenylethyl)amino)1-oxo-3-phenylpropan-2-yl)carbamoyl)benzoic acid analogues as BMP-2 stimulators", Journal of Medicinal Chemistry, vol. 55, No. 19, Sep. 14, 2012 (Sep. 14, 2012) pp. 8248-8259.
T.V. Magee, "Progress in discovery of small-molecule modulators of protein-protein interactions via fragment scree", Bioorganic & Medicinal Chemistry Letters, vol. 25, No. 12, May 2, 2015 (May 2, 2015) pp. 2461-2468.
D.E. Scott, et al., "Small-molecule inhibitors that target protein-protein interactions in the RAD51 family of recombinases", CHEMMEDCHEM, vol. 10, No. 2, Dec. 2, 2014 (Dec. 2, 2014), pp. 296-303.
M.E. Kavanagh, et al. "Substrate fragmentation for the design of M. tuberculosis CYP121 inhibitors", CHEMMEDCHEM, vol. 11, No. 17, Jul. 19, 2016 (Jul. 19, 2016), pp. 1924-1935.
Chandgude Ajay L. et al., "N-hydroxymide Ugi reaction toward [alpha]-hydrazino amides", Organic Letters, vol. 19, No. 5, Feb. 21, 2017 (Feb. 21, 2017) pp. 1228-1231.
Extended European Search Report issued in related European Patent Application No. 18848966.0 on Apr. 7, 2021.
Registry [online], Jul. 10, 2008 to Jan. 1, 2016, [Retrieved on Jul. 14, 2022], Retrieved from: STN, CAS Registry Nos. 1623325-56-3, 1623265-12-2, 1623261-37-9, 1277281-95-4, 1922704-71-9, 1833443-65-4, 1831083-82-9, 1647655-98-8, 1623303-78-5, 1575140-02-1, 1573376-01-8, 1571474-83-3, 1569908-74-2, 1569862-44-7, 1322984-18-8, 1299797-64-0, 1297834-09-3, 1286627-71-1, 1280060-22-1, 1277409-38-7, 1277364-25-6, 1277287-37-2, 1277042-04-2, 1276936-70-9.
Cuny, G. et al., Palladium- and Copper-Catalyzed Synthesis of Medium- and Large-Sized Ring-Fused Dihydroazaphenanthrenes and 1,4-Benzodiazepine-2,5-diones. Control of Reaction Pathway by Metal-Switching, Journal of the American Chemical Society, 2004, vol. 126, No. 44, p. 14475-14484.

* cited by examiner

DUAL ACTING FKBP12 AND FKBP52 INHIBITORS

CROSS REFERENCE TO RELATED APPLICATIONS

This application is a National Phase Application claiming benefit to International Patent Appl. No. PCT/US2018/047274, entitled "Dual Acting FKBP12 and FKBP52 Inhibitors," filed Aug. 21, 2018, which claims the benefit under 35 U.S.C. § 119 of U.S. Provisional Patent Appl. Nos. 62/547,976, entitled "Benzimidazole Derivatives as Dual Acting FKBP12 and FKBP52 Inhibitors" and 62/547,977, entitled "Dual Acting FKBP12 and FKBP52 Inhibitors," each filed on Aug. 21, 2017. The disclosures of these applications are incorporated herein by reference in their entireties.

BACKGROUND

Parkinson's disease (PD) is the second most common neurodegenerative disorder after Alzheimer's disease. In the US alone, 50,000-60,000 new cases of PD are diagnosed each year adding to the approximately one million patients who are currently living with PD. Importantly, no treatment is currently available that either stops or reverses neuronal degeneration in PD.

Parkinson's disease (PD) is characterized by the degeneration of dopaminergic neurons in the substantia nigra. A hallmark of PD neuronal degeneration is aberrant aggregation of alpha-synuclein (α-SYN). In PD, the protein is present in a fibrillar, aggregated form inside cytoplasmic inclusions called Lewy bodies. Enzymes of the FK506 binding protein (FKBP) family accelerate the aggregation of recombinant α-SYN in vitro and FK506, a specific FKBP inhibitor, abrogates this effect (Gerard et al., 2006, 2008).

FKBPs are members of the immunophilin family of proteins. These proteins are enzymes with peptidyl-prolyl cis-trans isomerase (PPIase) activity and bind to immunosuppressants such as FK506 (Göthel and Marahiel, 1999). PPIase enzymes catalyze cis-trans isomerization of X-Pro peptide bonds, an essential and rate-limiting step in the process of protein folding. The human FKBP family contains 15 principal members with many different functions (Galat, 2003; Rulten et al., 2006). Among these, four members, namely, FKBP12, FKBP38, FKBP52, and FKBP65, are enriched in the human brain (Steiner et al., 1992; Charters et al., 1994 a, b). Importantly, numerous clinical and pre-clinical studies have demonstrated that two FKPBs, FKBP12 and FKPB52, are involved in PD pathology. Recent experimental studies have shown that FKBP12 and FKBP52 potently accelerate formation of α-SYN aggregates present in Lewy bodies (LB), a hallmark of PD pathology (Deleersnijder, A. et al., 2011; and Gerard, M. et al., 2011). Immunophillins other than FKBP12/52, including FKBP 38, FKBP 51, and FKBP 65 are also enriched in brain and accelerate α-SYN aggregation, but to a lesser degree (Chattopadhaya, S. et al., 2012). In neuronal model of synucleinopathy, FKBP12/52 knockdown or inhibition by FK506 (a potent immunosuppressant inhibitor of FKBPs) could counter the effects of oxidative stress, while their overexpression enhanced α-SYN aggregation (Deleersnijder, A. et al., 2011; Gerard, M. 2010).

Their modulation not only promotes regeneration of the spared dopaminergic (DA) neurons, but also protects existing neurons from further neurodegeneration. Homology based sequence alignment of the FK506 binding domain of FKBP12 and FKBP52 show an overall identity of 53%. Interestingly, a closer analysis based on structural superposition reveals the identity to be as high as 82% within an 8 Å radius of the ligand binding site.

Given that no treatment is currently available for stopping or reversing neuronal degeneration in PD, there is a need to develop novel therapeutic agents that can protect against such degeneration.

SUMMARY

It has now been found that the compounds described herein and pharmaceutically acceptable compositions thereof are effective dual acting inhibitors of FKBP12 and FKBP52. Such compounds include those of formulas (I) and (II) below:

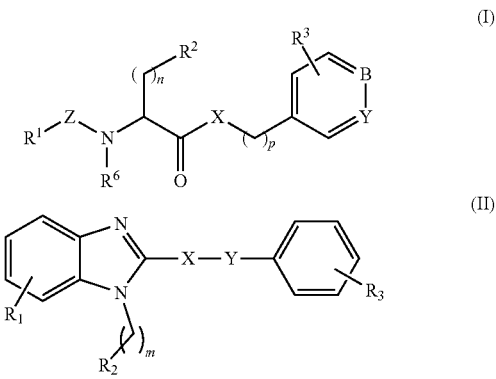

or a pharmaceutically active salt thereof, wherein $R^1$, $R^2$, $R^3$, $R^6$ in formula (I) and $R_1$, $R_2$ and $R_3$ in formula (II) are as defined herein.

The provided compounds and pharmaceutically acceptable compositions thereof are dual acting inhibitors of FKBP12 and FKBP52 and are useful for treating Parkinson's disease.

The provided compounds can be used alone (i.e., as a monotherapy) or in combination with one or more other therapeutic agents effective for treating Parkinson's disease.

The details of the invention are set forth in the description below. Other features, objects, and advantages of the invention will be apparent from the following detailed description of several embodiments, and from the appended claims.

DETAILED DESCRIPTION

1. General Description of Compounds

Figure 1A:
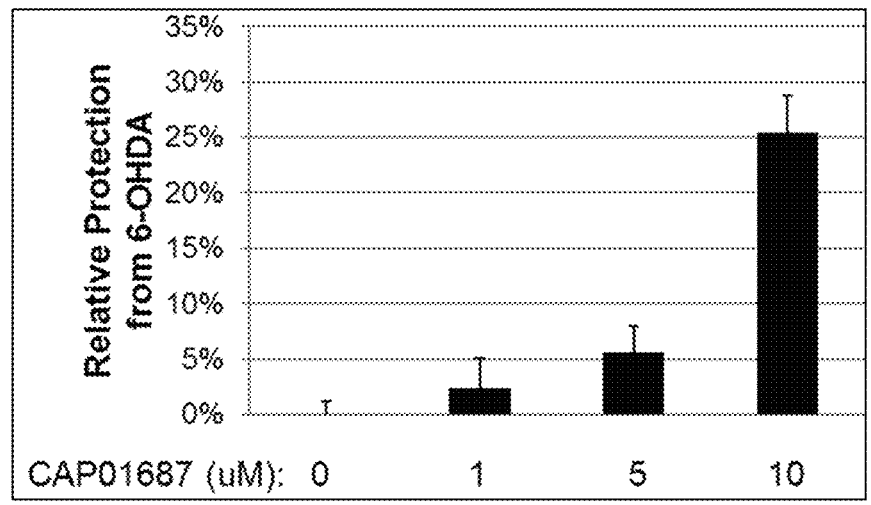
FIGS. 1A and 1B are a set of two bar graphs showing neuroprotection resulting from the administration of dual acting FKBP12 and FKBP52 inhibitory exemplary compounds CAP01687 (FIG. 1A) and CAP01693 (FIG. 1B) to PC12 rat pheochromocytoma cells, PC12, in a model of 6-hydroxydopamine (6-OHDA) induced Parkinson's disease.

In certain embodiments, the present disclosure provides a compound of Formula (I):

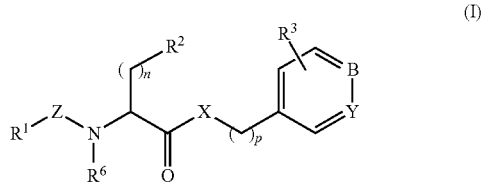

(I)

or a pharmaceutically acceptably salt thereof, wherein
$R^1$ is a cycloalkyl, aryl, or a heteroaryl group, optionally substituted with one or more groups independently selected from $R^4$; $(C_1-C_6)$alkyl; halo$(C_1-C_6)$ alkyl; $(C_2-C_6)$alkenyl; halo$(C_2-C_6)$ alkenyl; $(C_2-C_6)$alkynyl; halo $(C_2-C_6)$alkynyl; $(C_1-C_6)$alkoxy; halo$(C_1-C_6)$ alkoxy; $(C_1-C_6)$alkylthio; halo$(C_1-C_6)$alkylthio; $(C_1-C_6)$alkylsulfinyl; halo$(C_1-C_6)$ alkylsulfinyl; $(C_3-C_6)$cycloalkylsulfinyl; halo$(C_3-C_6)$cycloalkylsulfinyl; $(C_1-C_6)$alkylsulfonyl; halo$(C_1-C_6)$ alkylsulfonyl; $(C_3-C_6)$ cycloalkylsulfonyl; halo$(C_3-C_6)$cycloalkylsulfonyl; $(C_1-C_6)$alkylamino; di$(C_1-C_6)$alkylamino; $(C_1-C_6)$alkoxy$(C_1-C_6)$alkoxy; halo$(C_1-C_6)$alkoxy$(C_1-C_6)$alkoxy; $(C_1-C_6$ alkoxycarbonyl; aminocarbonyl; $H_2NSO_2$; $(C_1-C_6)$alkylaminocarbonyl; di$(C_1-C_6)$alkylaminocarbonyl; $(C_1-C_3)$alkoxy$(C_1-C_3)$alkylaminocarbonyl; heterocyclylcarbonyl; $(C_1-C_6)$alkylaminosulfonyl, di$(C_1-C_6)$ alkylaminosulfonyl; heterocyclylsulfonyl; $(C_1-C_6)$ alkylcarbonylamino; $(C_1-C_6)$alkylcarbonylamino$(C_1-C_6)$alkyl; $(C_1-C_6)$alkylsulfonylamino; $(C_1-C_6)$alkylsulfonylamino$(C_1-C_6)$ alkyl; $(C_1-C_6)$alkoxycarbonyl$(C_1-C_6)$alkoxy; $(C_1-C_6)$ alkoxy$(C_1-C_6)$alkyl, halo$(C_1-C_6)$ alkoxy$(C_1-C_6)$alkyl; hydroxy$(C_1-C_6)$alkoxy; amino$(C_1-C_6)$alkyl; $(C_1-C_6)$alkylamino$(C_1-C_6)$alkyl; di$(C_1-C_6)$alkylamino$(C_1-C_6)$alkyl; $(C_1-C_6)$alkylamino$(C_2-C_6)$alkoxy; di$(C_1-C_6)$alkylamino$(C_2-C_6)$alkoxy; $(C_1-C_6)$alkylcarbonyl; hydroxy $(C_1-C_6)$alkylcarbonyl; $(C_1-C_6)$alkylhydroxycarbonyl; $(C_1-C_6)$alkylhydroxy$(C_1-C_6)$alkyl; $(C_3-C_6)$cycloalkylcarbonyl; $(C_3-C_6)$cycloalkylaminocarbonyl; $\{(C_3-C_6)$ cyclo alkyl$\}\{(C_1-C_6)$alkyl$\}$aminocarbonyl; di$(C_3-C_6)$ cycloalkylaminocarbonyl; $(C_3-C_6)$cycloalkylaminosulfonyl; $\{(C_3-C_6)$cycloalkyl$\}$ $\{(C_1-C_6)$ alkyl$\}$aminosulfonyl; di$(C_3-C_6)$cycloalkylaminosulfonyl; cyano$(C_1-C_6)$alkyl; amino carbonyl$(C_1-C_6)$alkyl; $(C_1-C_6)$alkylaminocarbonyl$(C_1-C_6)$alkyl; di$(C_1-C_6)$alkylaminocarbonyl$(C_1-C_6)$alkyl; $(C_3-C_6)$cycloalkylaminocarbonyl$(C_1-C_6)$alkyl; $\{(C_3-C_6)$cycloalkyl$\}$ $\{(C_1-C_6)$alkyl$\}$ amino carbonyl$(C_1-C_6)$alkyl; $[C_1-C_6)$alkyl $(C_4-C_6)$heterocyclyl]$(C_1-C_6)$alkyl; and di$(C_3-C_6)$ cycloalkylaminocarbonyl$(C_1-C_6)$alkyl;

$R^2$ is a cycloalkyl or an aromatic ring optionally substituted with one or more groups independently selected from $R^5$;

$R^3$, $R^4$, and $R^5$ are independently selected from halo; cyano; nitro; amino; hydroxy; carboxy; $(C_1-C_6)$alkyl; halo$(C_1-C_6)$ alkyl; $(C_1-C_6)$hydroxyalkyl; $(CH_2)_{1-3}$ COOH; $(C_1-C_6)$ alkoxy; halo$(C_1-C_6)$alkoxy; $(C_1-C_6)$ alkylthio; halo$(C_1-C_6)$alkylthio; $(C_1-C_6)$alkylsulfinyl; halo$(C_1-C_6)$alkylsulfinyl; $(C_1-C_6)$alkylsulfonyl; halo $(C_1-C_6)$alkylsulfonyl; $(C_1-C_6)$alkylamino; di$(C_1-C_6)$ alkylamino; $(C_2-C_4)$alkoxycarbonyl; $(C_2-C_4)$alkylaminocarbonyl; di$(C_2-C4)$alkylaminocarbonyl; $(C_3-C_6)$cycloalkyl; halo$(C_3-C_6)$cycloalkyl; $(C_3-C_6)$cycloalkoxy; halo$(C_3-C_6)$cycloalkoxy; aryl optionally substituted with halogen, OH, or $NH_2$; aryloxy; $(C_1-C_6)$alkylthio; halo$(C_1-C_6)$alkylthio; $(C_3-C_6)$cycloalkylthio; halo$(C_3-C_6)$cycloalkylthio; $(C_1-C_6)$alkylamino; and di$(C_1-C_6)$ alkylamino groups.

$R^6$ is hydrogen, $(C_1-C_6)$alkyl, or halo$(C_1-C_6)$alkyl;

X is O or NH;

Z is $CH_2$ or C=O n is a number from 0 to 4;

p is a number from 1 to 5;

B and Y are independently CH or N.

In certain other embodiments, the present disclosure provides a compound of Formula (II):

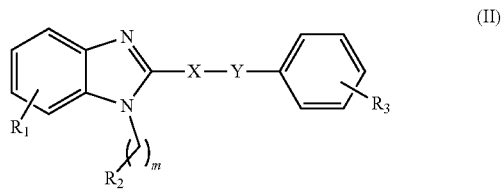

(II)

or a pharmaceutically acceptable salt thereof,
wherein each of $R_1$ and $R_3$ is independently selected from the group consisting of hydrogen; halogen; nitro; cyano; amino; hydroxy; carboxy; $(C_1-C_6)$alkyl; halo $(C_1-C_6)$alkyl; $(C_1-C_6)$alkoxy; halo$(C_1-C_6)$alkoxy; $(C_3-C_{10})$cycloalkyl; halo$(C_3-C_{10})$cycloalkyl; $(C_3-C_{10})$cycloalkylthio; halo$(C_3-C_{10})$cycloalkylthio; $(C_3-C_{10})$ heterocycloalkyl; halo(C₃-C₁₀)heterocycloalkyl; (C₁-C₆)alkylamino; di(C₁-C₆)alkylamino; (C₁-C₆)alkylthio; halo(C₁-C₆)alkylthio; (C₁-C₆)alkylsulfinyl; halo(C₁-C₆)alkylsulfinyl; (C₁-C₆)alkylsulfonyl; halo (C₁-C₆)alkylsulfonyl; (C₃-C₁₀)cycloalkylsulfinyl; halo (C₃-C₁₀)cycloalkylsulfinyl; (C₃-C₁₀)cycloalkylsulfonyl; halo(C₃-C₁₀)cycloalkylsulfonyl; aryl, heteroaryl, arylamine, or heterocyclyl, optionally substituted with halogen, nitro, cyano, amino, hydroxy, carboxy, (C₁-C₆)alkyl, halo(C₁-C₆)alkyl, (C₁-C₆)alkoxy, or halo(C₁-C₆)alkoxy; and an aryl ring fused to the relevant phenyl ring, either ring being optionally substituted with halogen, nitro, cyano, amino, hydroxy, carboxy, (C₁-C₆)alkyl, halo(C₁-C₆)alkyl, (C₁-C₆)alkoxy, halo(C₁-C₆)alkoxy or arylamine;

X—Y is C=C, C≡C, or N=N;

R₂ is selected from the group consisting of (C₁-C₆)alkyl; halo(C₁-C₆)alkyl; (C₂-C₆)alkenyl; halo(C₂-C₆)alkenyl; (C₂-C₆)alkynyl; halo(C₂-C₆)alkynyl; (C₃-C₁₀)cycloalkyl; halo(C₃-C₁₀)cycloalkyl; heterocyclyl, aryl, or heteroaryl, each optionally substituted with one or more groups independently selected from halogen, nitro, cyano, amino, hydroxy, carboxy, (C₁-C₆)alkyl, halo (C₁-C₆)alkyl, (C₁-C₆)alkoxy, and halo(C₁-C₆)alkoxy; and m is 0 to 4.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The terms "cycloalkyl" used alone or as part of a larger moiety, refers to a saturated cyclic aliphatic monocyclic, bicyclic or tricyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. Bicyclic cycloalkyl groups include e.g., cycloalkyl group fused to another cycloalkyl group, such as decalin or a cycloalkyl group fused to an aryl group (e.g., phenyl) or heteroaryl group, such as tetrahydronaphthalenyl, indanyl, 5,6,7,8-tetrahydroquinoline, and 5,6,7,8-tetrahydroisoquinoline. An example of a tricyclic ring system is adamantane. It will be understood that the point of attachment for bicyclic cycloalkyl groups can be either on the cycloalkyl portion or on the aryl group (e.g., phenyl) or heteroaryl group that results in a stable structure. It will be further understood that when specified, optional substituents on a cycloalkyl may be present on any substitutable position and, include, e.g., the position at which the cycloalkyl is attached.

The term "heterocyclyl" means a 4-, 5-, 6- and 7-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", may be used interchangeably. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxetanyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocyclyl group may be mono or bicyclic. Unless otherwise specified, bicyclic heterocyclyl groups include, e.g., unsaturated or saturated heterocyclic radicals fused to another unsaturated heterocyclic radical or aromatic or heteroaryl ring, such as for example, chromanyl, 2,3-dihydrobenzo[b][1,4]dioxinyl, tetrahydronaphthyridinyl, indolinonyl, dihydropyrrolotriazolyl, imidazopyrimidinyl, quinolinonyl, dioxaspirodecanyl. It will be understood that the point of attachment for bicyclic heterocyclyl groups can be on the heterocyclyl group or aromatic ring that results in a stable structure. It will also be understood that when specified, optional substituents on a heterocyclyl group may be present on any substitutable position and, include, e.g., the position at which the heterocyclyl is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. A heteroaryl group may be mono- or bicyclic. It will be understood that when specified, optional substituents on a heteroaryl group may be present on any substitutable position and, include, e.g., the position at which the heteroaryl is attached.

As used herein, the term "aryl", used alone or in conjunction with other terms, refers to a 6-14 membered aromatic ring containing only ring carbon atoms. The aryl ring may be monocyclic, bicyclic, or tricyclic. Non-limiting examples include phenyl, naphthyl, biphenyl, anthracenyl, and the like. It will also be understood that when specified, five optional substituents on an aryl group may be present on any substitutable position. In an embodiment, the aryl group is unsubstituted or mono- or di-substituted.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts. Pharmaceutically acceptable basic/cationic salts include, the sodium, potassium, calcium, magnesium, diethanolamine, n-methyl- D-glucamine, L-lysine, L-arginine, ammonium, ethanolamine, piperazine, and triethanolamine salts. Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of neurodegenerative disorders. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

3. Description of Exemplary Compounds

In a first embodiment, the present disclosure provides a compound of Formula (I)

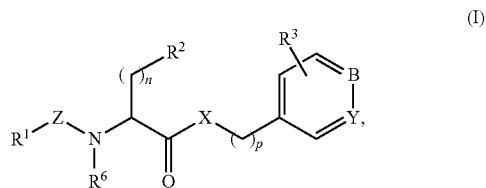

or a pharmaceutically acceptable salt thereof, wherein the variables are as described above.

In a second embodiment, a compound of embodiment 1 is provided, wherein n is 0, 1, or 2.

In a third embodiment, a compound of embodiment 1 is provided, wherein, n is 0, 1, or 2, and p is 2 or 3.

In a fourth embodiment a compound of embodiment 3 is provided, wherein B and Y are CH.

In a fifth embodiment, a compound of embodiment 4 is provided, wherein $R^2$ is a cycloalkyl group.

In a sixth embodiment, a compound of embodiment 5 is provided, wherein the cycloalkyl group has five or six ring carbon atoms.

In a seventh embodiment, a compound of embodiment 4 is provided, wherein $R^2$ is an aryl group.

In an eighth embodiment, a compound of embodiment 7 is provided, wherein the aryl group is a phenyl group.

In a ninth embodiment, a compound of embodiment 8 is provided, wherein n is 1 or 2.

In a tenth embodiment, a compound of any of embodiments 1 to 9 is provided, wherein $R^5$ is a halogen.

In an eleventh embodiment, a compound of any of embodiments 1 to 9 is provided, wherein $R^1$ is a cycloalkyl group.

In a twelfth embodiment, a compound of embodiment 11 is provided, wherein the cycloalkyl group is an adamantane.

In a thirteenth embodiment, a compound of any of embodiments 1 to 9 is provided, wherein $R^1$ is an aryl group.

In a fourteenth embodiment, a compound of embodiment 13 is provided, wherein the aryl group is a napthyl group.

In a fifteenth embodiment, a compound of embodiment 13 is provided, wherein $R^4$ is a halogen.

In a sixteenth embodiment, a compound of embodiment 13 is provided, wherein $R^1$ is napthyl and $R^4$ is halogen.

In a seventeenth embodiment, a compound of embodiment 13 is provided, wherein $R^4$ is a $C_1$-$C_6$ alkoxy group.

In an eighteenth embodiment, a compound of embodiment 17 is provided, wherein $R^4$ is a methoxy group.

In a nineteenth embodiment, a compound of any of embodiments 1 to 9 is provided, wherein $R^1$ is an indazole group.

In a twentieth embodiment, a compound of embodiment 19 is provided, wherein $R^4$ is an aryl group.

In a twenty first embodiment, a compound of any of embodiments 1 to 9 is provided, wherein $R^1$ is an indole group.

In a twenty second embodiment, a compound of any of embodiments 1 to 9 is provided, wherein $R^1$ is a phenyl substituted aryl group.

In a twenty third embodiment, a compound of any of embodiments 1 to 9 is provided, wherein $R^1$ is a phenoxy substituted aryl group.

In a twenty fourth embodiment, a compound of any of embodiments 1 to 9 is provided, wherein $R^1$ is a benzimidazole group.

In a twenty fifth embodiment, a compound of any one of embodiments 1 to 9 is provided, wherein $R^3$ is H, $R^4$ is a halogen or a $C_1$-$C_6$ alkoxy, and $R^5$ is a halogen.

In a twenty sixth embodiment, a compound of embodiment 19 is provided, wherein $R^3$ is H, $R^4$ is a halogen or a $C_1$-$C_6$ alkoxy, and $R^5$ is a halogen.

In a twenty seventh embodiment, a compound of embodiment 21 is provided, wherein $R^3$ is H, $R^4$ is a halogen or a $C_1$-$C_6$ alkoxy, and $R^5$ is a halogen.

In a twenty eighth embodiment, a compound of embodiment 22 is provided, wherein $R^3$ is H, $R^4$ is a halogen or a $C_1$-$C_6$ alkoxy, and $R^5$ is a halogen.

In a twenty ninth embodiment, a compound of embodiment 23 is provided, wherein $R^3$ is H, $R^4$ is a halogen or a $C_1$-$C_6$ alkoxy, and $R^5$ is a halogen.

In a thirtieth embodiment, a compound of embodiment 24 is provided, wherein $R^3$ is H, $R^4$ is a halogen or a $C_1$-$C_6$ alkoxy, and $R^5$ is a halogen.

In a thirty first embodiment, a compound of any of embodiments 1 to 3 is provided, wherein B is CH and Y is N.

In a thirty second embodiment, a compound of embodiment 31 is provided, wherein $R^1$ is an aryl group.

In a thirty third embodiment, a compound of embodiment 32 is provided, wherein the aryl group is a napthyl.

In a thirty fourth embodiment, a compound of embodiment 33 is provided, wherein $R^2$ is an aryl group.

In a thirty fifth embodiment, a compound of embodiment 34 is provided, wherein $R^4$ is a halogen.

In a thirty sixth embodiment, a compound of embodiment 34 is provided, wherein $R^5$ is a halogen.

In a thirty seventh embodiment, a compound of embodiment 36 is provided, wherein each of $R^4$ and $R^5$ is a halogen.

In a thirty eighth embodiment, a compound of embodiment 31 is provided, wherein $R^2$ is a cycloalkyl group.

In a thirty ninth embodiment, a compound of embodiment 38 is provided, wherein the cycloalkyl group has five or six ring carbon atoms.

In a fortieth embodiment, a compound of embodiment 31 is provided, wherein X is O and $R^1$ is a branched five carbon alkyl group.

In a forty first embodiment, a compound having a formula selected from

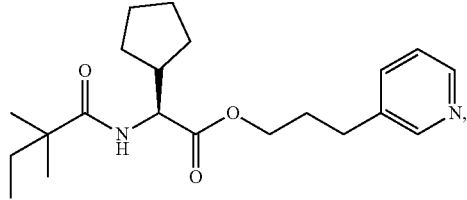

-continued

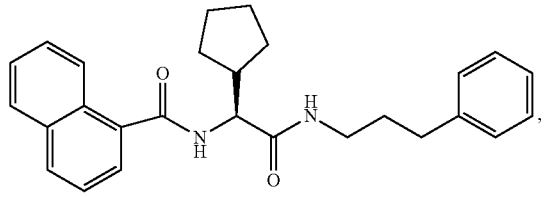

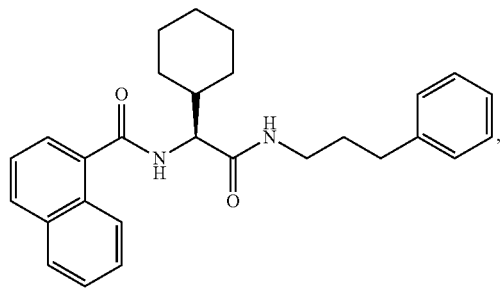

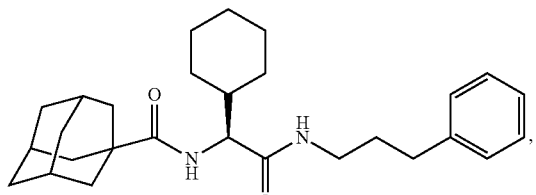

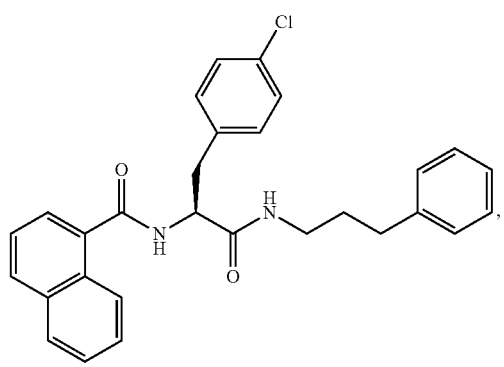

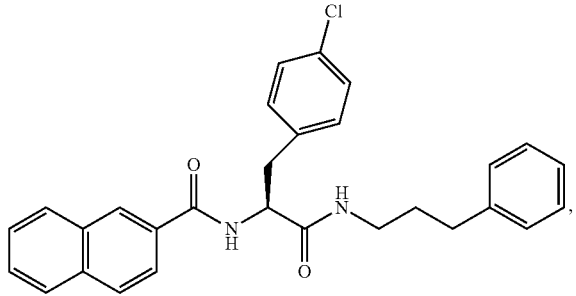

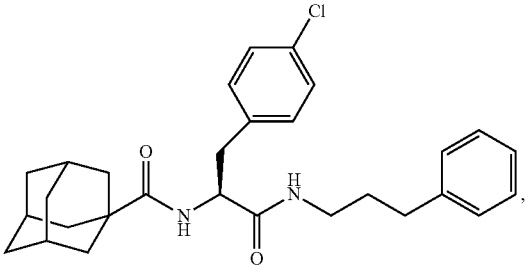

-continued
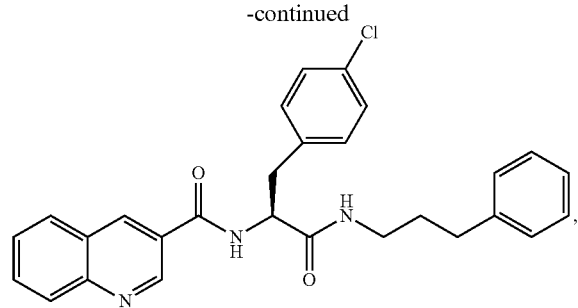
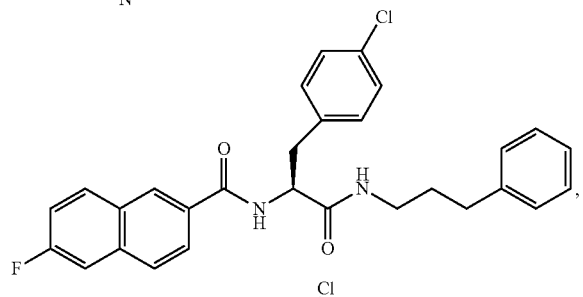
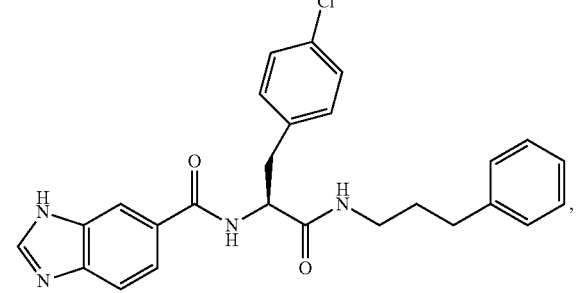
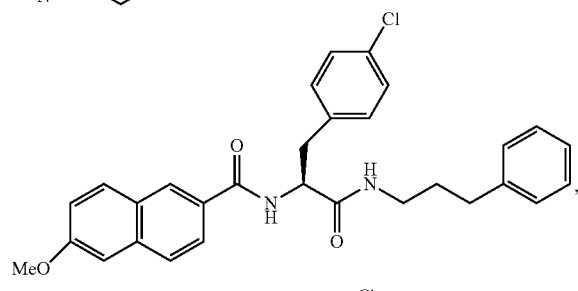
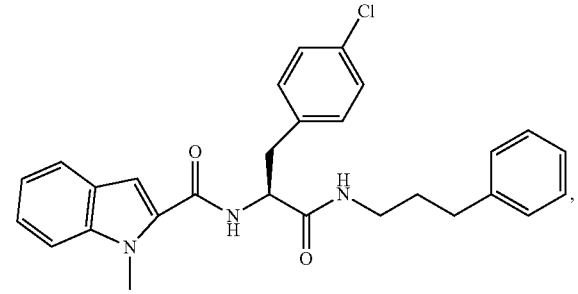
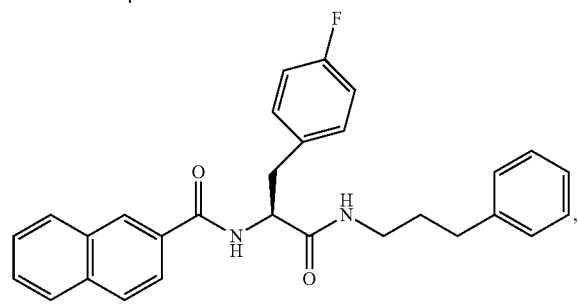
-continued
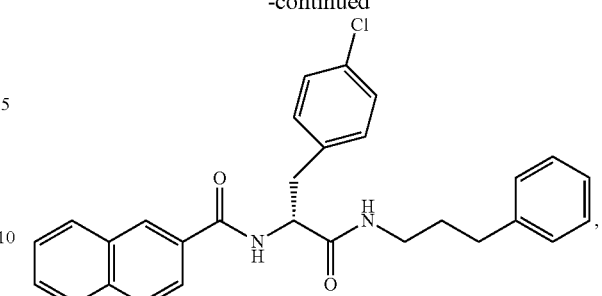
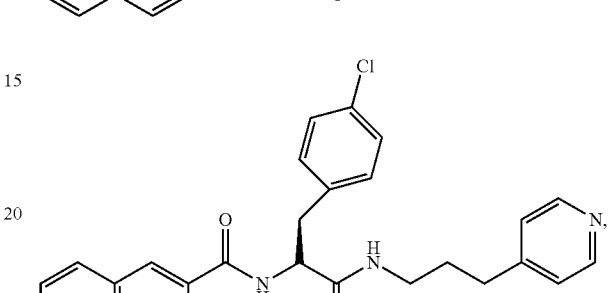
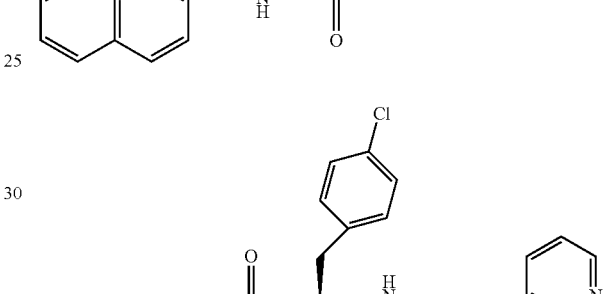
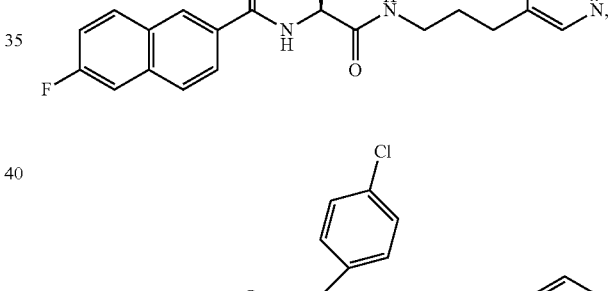
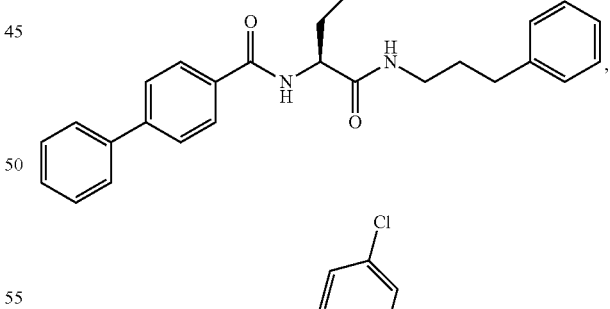
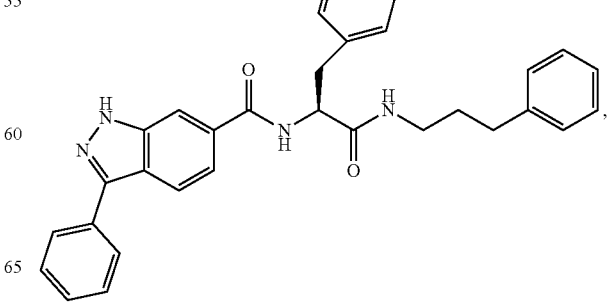

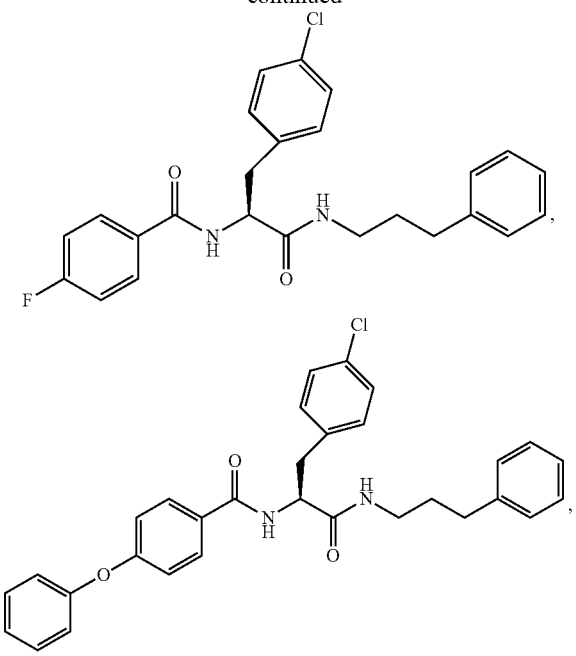

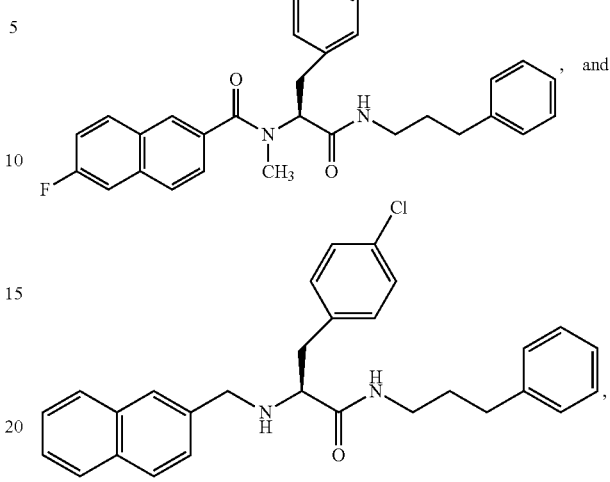

or a pharmaceutically acceptably salt thereof is provided.

In a forty second embodiment, the disclosure provides a pharmaceutical composition comprising a compound according to any of embodiments 1-41, or a pharmaceutically acceptable salt thereof, and an acceptable carrier.

In a forty third embodiment, the disclosure provides a method of treating Parkinson's disease in a subject, the method comprising administering to the subject a therapeutically effective amount of a compound according to any one of embodiments 1-41, or a pharmaceutically acceptable salt thereof.

In a forty fourth embodiment the disclosure provides a pharmaceutical composition for nasal administration comprising a compound according to any of the embodiments 1 to 41 or a pharmaceutically acceptable salt thereof, combined with a lipid and a non-ionic surfactant and an effective amount of an absorption promoting agent to allow nasal absorption of a pharmacologically effective amount of the compound.

In a forty fifth embodiment, a composition according to embodiment 44 is provided, wherein the absorption promoting agent is a cationic polymer.

In a forty sixth embodiment, a composition according to embodiment 45 is provided, wherein the cationic polymer is chitosan.

In a forty seventh embodiment, a method of treating Parkinson's disease in a subject is provided, the method comprising administering to the subject a therapeutically effective amount of a pharmaceutical composition for nasal administration comprising a compound according to any of the embodiments 1 to 41 or a pharmaceutically acceptable salt thereof, combined with a lipid and a non-ionic surfactant and an effective amount of an absorption promoting agent to allow nasal absorption of a pharmacologically effective amount of the compound.

In a forty eighth embodiment, a method according to embodiment 47 is provided, wherein the absorption promoting agent is a cationic polymer.

In a forty ninth embodiment, a method according to embodiment 48 is provided, wherein the cationic polymer is chitosan.

In a fiftieth embodiment, the present disclosure provides a compound of Formula (II)

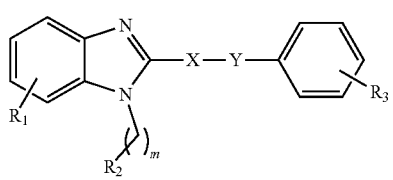

(II)

or a pharmaceutically acceptable salt thereof, wherein the variables are as described above.

In a fifty first embodiment, the present disclosure provides a compound of embodiment 1, wherein 1, wherein X—Y is C=C, m is 0 to 3, and $R^2$ is an aryl, optionally substituted with halogen, $(C_1-C_6)$alkyl, halo$(C_1-C_6)$alkyl, $(C_1-C_6)$alkoxy, or halo$(C_1-C_6)$alkoxy.

In a fifty second embodiment, a compound according to embodiment 51 is provided, wherein the aryl is a phenyl, optionally substituted with halogen, $(C_1-C_6)$alkyl, or halo$(C_1-C_6)$alkyl.

In a fifty third embodiment, a compound according to embodiment 50 is provided, wherein X—Y is C=C, m is 1, $R_2$ is $(C_2-C_6)$alkenyl, or $C_2-C_6$)alkynyl.

In a fifty fourth embodiment, the disclosure provides a compound of embodiment 53, wherein $R_2$ is $(C_2-C_6)$alkenyl.

In a fifty fifth embodiment, a compound according to embodiment 53 is provided, wherein $R_2$ is $(C_2-C_6)$alkynyl.

In a fifty sixth embodiment, the present disclosure provides a compound of embodiment 51, wherein $R_3$ is $(C_1-C_6)$alkylamino, or di$(C_1-C_6)$alkylamino.

In a fifty seventh embodiment, a compound according to embodiment 56 is provided, wherein $R_3$ is di$(C_1-C_6)$alkylamino.

In a fifty eighth embodiment, the disclosure provides a compound of embodiment 57, wherein $R_3$ is $N(CH_3)_2$.

In a fifty ninth embodiment, a compound of embodiment 56 is provided, wherein $R_2$ is $(C_1-C_6)$alkyl.

In a sixtieth embodiment, a compound according to embodiment 51 is provided, wherein m is 0 to 2, $R_3$ is halogen and $R_2$ is $(C_1-C_6)$alkyl or halo$(C_1-C_6)$alkyl.

In a sixty first embodiment, a compound according to of embodiment 51 is provided, wherein $R_1$ is hydrogen.

In a sixty second embodiment, a compound according to embodiment 61 is provided, wherein $R_2$ is phenyl optionally substituted with halogen.

In a sixty third embodiment, a compound according to embodiment 53 is provided, wherein $R_1$ is hydrogen.

In a sixty fourth embodiment, a compound according to embodiment 63 is provided, wherein $R_2$ is $(C_2-C_6)$ alkenyl.

In a sixty fifth embodiment, a compound according to embodiment 56 is provided, wherein $R_1$ is hydrogen.

In a sixty sixth embodiment, a compound according to embodiment 65 is provided, wherein $R_3$ is di$(C_1-C_6)$ alkylamino.

In a sixty seventh embodiment, a compound according to embodiment sixty is provided, wherein $R_1$ is hydrogen.

In a sixty eighth embodiment, a compound having a formula selected from:

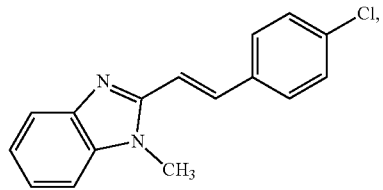

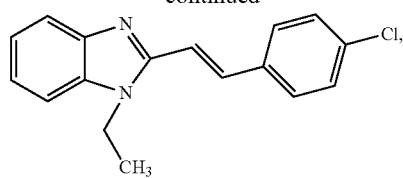

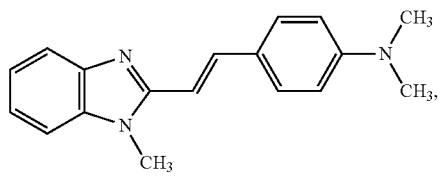

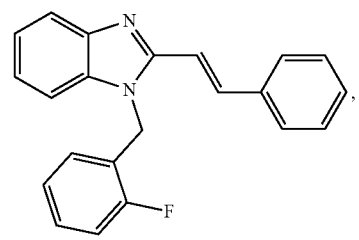

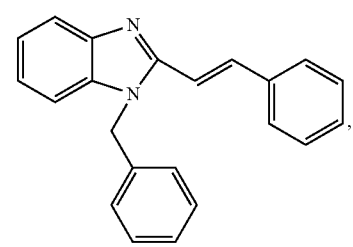

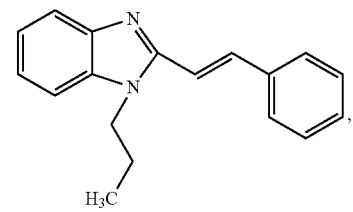

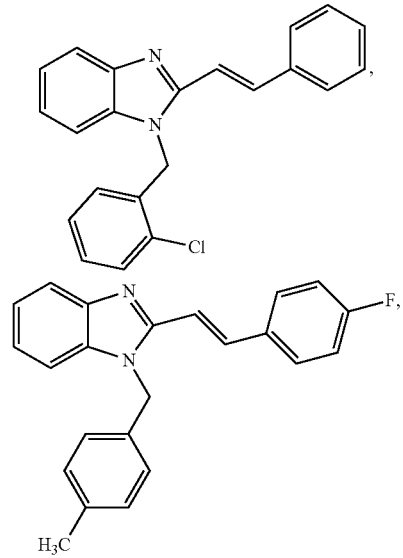

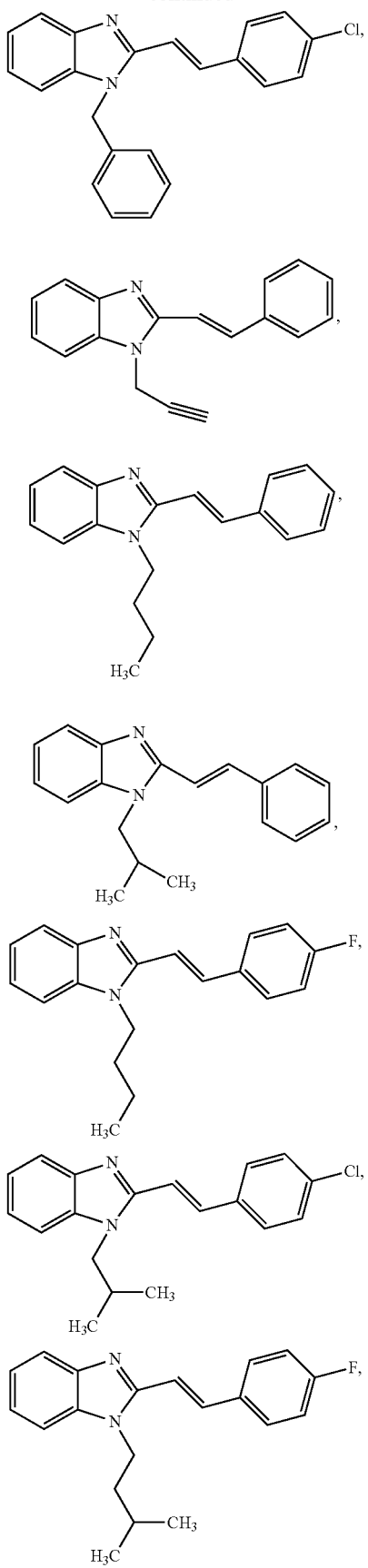
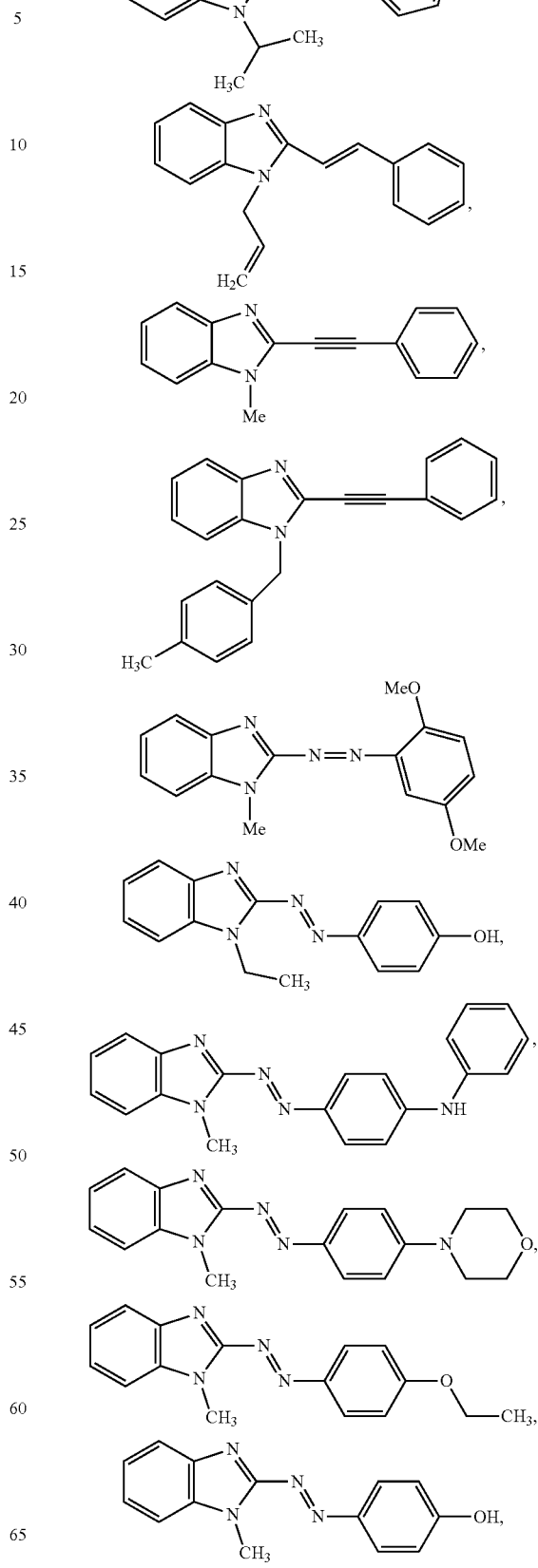

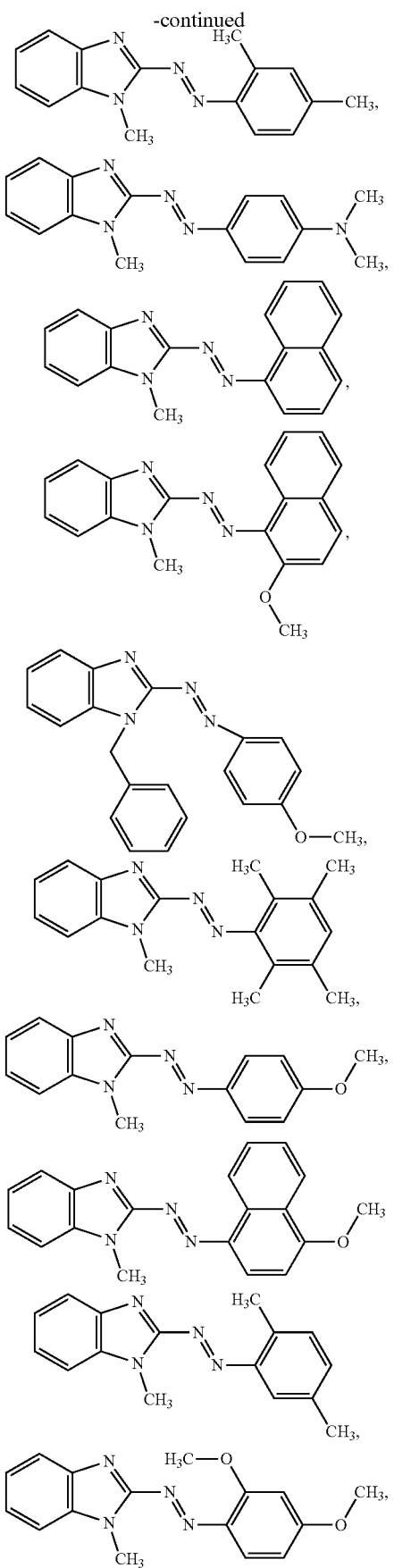

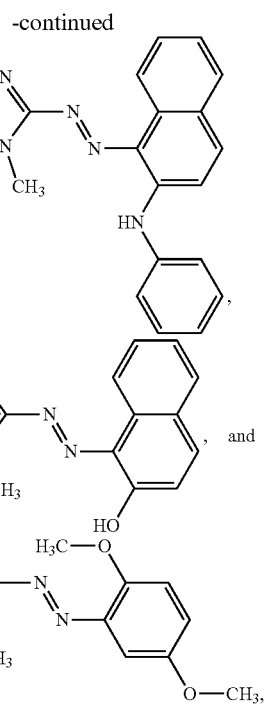

or a pharmaceutically acceptably salt thereof, is provided.

In a sixty ninth embodiment, the present disclosure provides a pharmaceutical composition comprising a compound according to any one of embodiments 50-68, a pharmaceutically acceptable salt thereof; and a pharmaceutically acceptable carrier.

In a seventieth embodiment, a method of treating Parkinson's disease in a subject is provided, the method comprising administering to the subject a therapeutically effective amount of a compound according to any one of embodiments 50-68, or a pharmaceutically acceptable salt thereof.

In a seventy first embodiment, the disclosure provides a pharmaceutical composition for nasal administration comprising a compound according to any of the embodiments 50-68 or a pharmaceutically acceptable salt thereof, combined with a lipid and a non-ionic surfactant and an effective amount of an absorption promoting agent to allow nasal absorption of a pharmacologically effective amount of the compound.

In a seventy second embodiment, a composition according to embodiment 71 is provided, wherein the absorption promoting agent is a cationic polymer.

In a seventy third embodiment, a composition of embodiment 72 is provided, wherein the cationic polymer is chitosan.

In a seventy fourth embodiment, a method of treating Parkinson's disease in a subject, comprising administering to the subject a therapeutically effective amount of a compound according to any one of embodiments 50-68 or a pharmaceutically acceptable salt thereof, combined with a lipid and a non-ionic surfactant and an effective amount of an absorption promoting agent to allow nasal absorption of a pharmacologically effective amount of the compound.

In a seventy fifth embodiment, a method of embodiment 74 is provided, wherein the absorption promoting agent is a cationic polymer.

In a seventy sixth embodiment, a method of embodiment 75 is provided, wherein the cationic polymer is chitosan.

In certain embodiments, the amount of the compounds of Formulas (I) or (II) in a provided composition is such that it is effective as a dual inhibitor of FKBP12 and FKBP52 in a biological sample or in a subject. In certain embodiments, a provided composition is formulated for administration to a subject in need of such composition. In some embodiments, a provided composition is formulated for oral administration to a subject. In certain embodiments, a provided composition is formulated for nasal administration to a subject.

4. Uses, Formulation, and Administration

Pharmaceutically Acceptable Compositions:

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Remington's Pharmaceutical Sciences Ed. by Gennaro, Mack Publishing, Easton, Pa., 1995 (the contents of which are hereby incorporated by reference), discloses various carriers used in formulating pharmaceutical compositions and known techniques for the preparation thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of an injectable formulation. Injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the compound in the composition.

Included within the scope of the invention is a pharmaceutical composition for nasal administration that includes a compound or a pharmaceutically acceptable salt thereof according to any of the embodiments 1-41 or 50-68 described above, combined with an effective amount of an absorption promoting agent to allow nasal absorption of a pharmacologically effective amount of the compound. Intranasal delivery is attractive as an alternative route for administration of drugs and biomolecules that are susceptible to enzymatic or acidic degradation, first-pass hepatic metabolism, and for overcoming problems of low brain bioavailability due to blood-brain barrier. As such, the composition is useful for treating neurodegenerative disease such as Alzheimer's and Parkinson's disease and cancers of the brain, e.g., Glioblastoma, primary malignant brain tumor, and malignant glioma. Nasally administered drugs have the advantage of access to a relatively large surface area for permeation (afforded by the large number of microvilli present in the nasal cavity), a porous endothelial membrane, and a highly-vascularized epithelium. Lipid and non-ionic surfactant based elastic vesicular delivery systems, which include an agent that promotes absorption to mucus membrane (e.g., a chitosan-based hybrid vesicular system), show enhanced permeability compared to conventional forms of dosing (solutions, suspensions, sprays, snuffs, emulsions, and gels). These vesicular delivery systems include both stabilizing and destabilizing molecules within a single bilayer wall, which provides elasticity and also allows the system to act as a barrier modulating agent. Intranasal route has proven to be a promising means for use of these delivery systems and allows intimate and prolonged contact between the drug carrier and the mucus membrane. In addition to enhanced permeability, the vesicles of the lipid and non-ionic surfactant based elastic vesicular delivery systems are highly stable and possess a high capacity for drug loading and a controlled release profile, all of which when taken into consideration, make them a good choice as carriers for both hydrophilic and lipophilic drug molecules.

Absorption promoting agents contemplated to be used in the composition for nasal administration described herein include a cationic polymer, a surface-active agent, a chelating agent, a mucolytic agent, a cyclodextrin, and combinations thereof. Further, cationic polymers that may be used include other polycationic carbohydrates such as but not limited to inorganic or organic salts of chitosan and modified forms of chitosan (especially more positively charged ones), polyaminoacids such as polylysine, polyquaternary compounds, protamine, polyamine, DEAE-imine, polyvinylpyridine, polythiodiethyl-aminomethylethylene (P(TDAE)), polyhistidine, DEAE-methacrylate, DEAE-acrylamide, poly-p-aminostyrene, polyoxethane, co-polymethacrylates (e.g. copolymers of HPMA, N-(2-hydroxypropyl)-methacrylamide, GAFQUAT (U.S. Pat. No. 3,910,862) and polyamidoamines. The polycationic substances used in the invention typically have a molecular weight of 10 000 or more. The chitosan (or salt thereof) preferably has an intrinsic viscosity of at least 400 ml/g, more preferably at least 500, 750 or 1000 ml/g.

5. Uses of Compounds and Pharmaceutically Acceptable Compositions

Compounds and compositions described herein are generally useful for dual inhibition of FKBP12 and FKBP52, which potently accelerate formation of α-SYN aggregates present in Lewy bodies (LB), a hallmark of Parkinson's disease pathology. Thus, in some embodiments, the present disclosure provides a method of treating Parkinson's disease, the method comprising administering a provided compound or composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

The disclosure further provides a method of treating a subject, such as a human, suffering from Parkinson's disease.

The disclosure further relates to the use of provided compounds for the production of pharmaceutical compositions which are employed for the treatment and/or prophylaxis and/or amelioration of Parkinson's disease.

Compounds or compositions described herein may be administered using any amount and any route of administration effective for treating or lessening the severity of Parkinson's disease. The exact amount required will vary from subject to subject, depending on the species, age, and general condition of the subject, the severity of the disease, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General:

Unless otherwise indicated, all anhydrous solvents were commercially obtained and stored in Sure-seal bottles under nitrogen. All other reagents and solvents were purchased as the highest grade available and used without further purification. Thin-layer chromatography (TLC) analysis of reaction mixtures was performed using Merck silica gel 60 F254 TLC plates, and visualized using ultraviolet light. NMR spectra were recorded on Bruker 500 MHz instrument. Chemical shifts ($\delta$) are reported in parts per million (ppm) referenced to $^1$H (Me$_4$Si at 0.00). Coupling constants (J) are reported in Hz throughout. Mass spectral data were acquired on Shimadzu LCMS-2010EV for low resolution, and on an Agilent ESI-TOF for either high or low resolution. Purity of all compounds was obtained in a HPLC Breeze from Waters Co. using an Atlantis T3 3 µm 4.6×150 mm reverse phase column. The eluant was a linear gradient with a flow rate of 1 ml/min from 95% A and 5% B to 5% A and 95% B in 15 min followed by 5 min at 100% B (Solvent A: H$_2$O with 0.1% TFA; Solvent B: acetonitrile with 0.1% TFA). The compounds were detected at $\lambda$=254 nm or 214 nm. Purity of key compounds was established by elemental analysis as performed on a Perkin Elmer series II-2400. Combustion analysis was performed by NuMega Resonance Labs, San Diego, CA, USA.

Synthesis:

Compounds according to Formula (I) can be prepared by art recognized techniques. Shown below in Examples 1-14 are structures of 14 exemplary compounds of Formula (I) and how they were prepared. The analytical data for the compounds thus prepared are also set forth in Examples 1-14 and the procedures for testing these compounds are described in Examples 15-17 that follow.

Compounds according to Formula (II) can be prepared by art recognized techniques using the following synthetic schemes:

Scheme 1

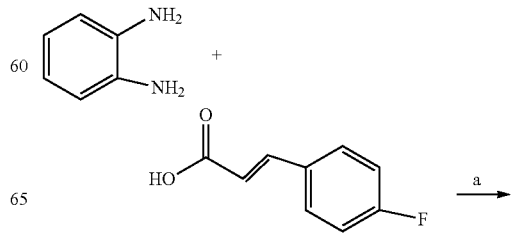

27
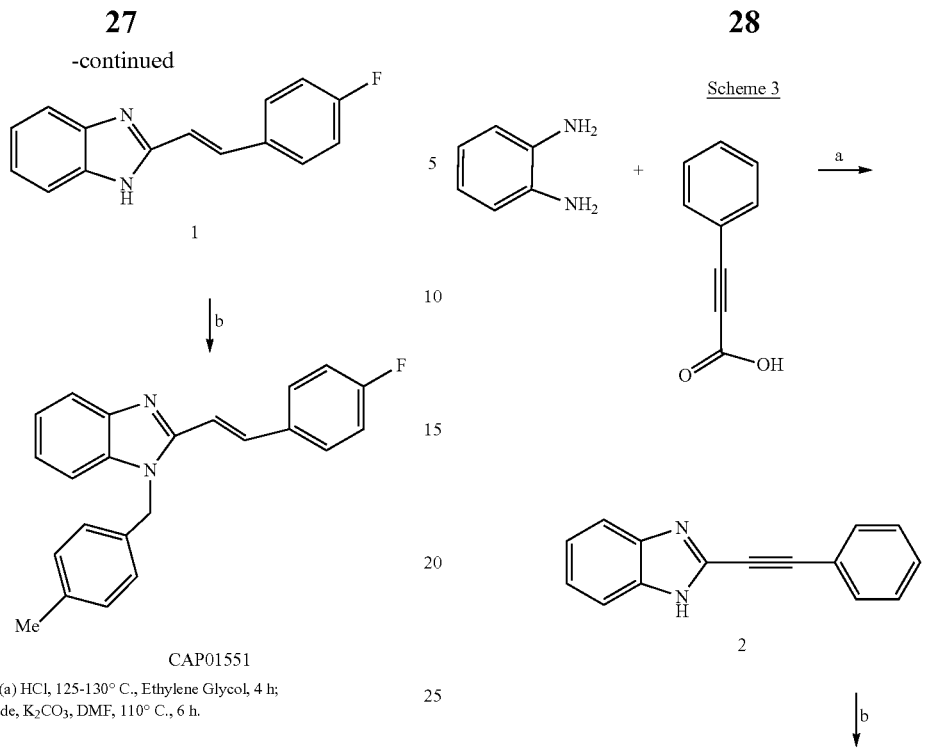
CAP01551
Reagents and conditions: (a) HCl, 125-130° C., Ethylene Glycol, 4 h; (b) 4-Methylbenzyl chloride, $K_2CO_3$, DMF, 110° C., 6 h.
28
Scheme 3
Scheme 2
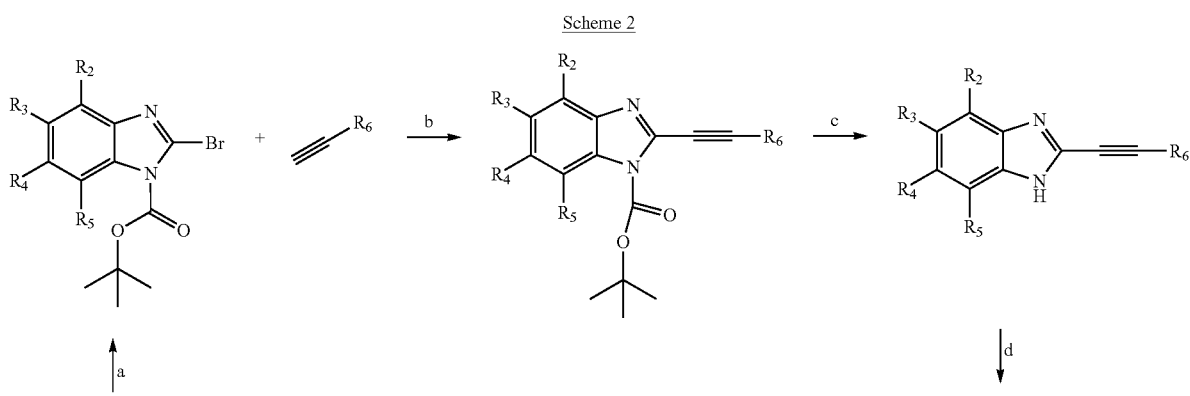
Reagents and conditions: (a) $Et_3N$, Boc-anhydride, $CH_3CN$, rt, 16 h.; (b) $Pd(Ph_3P)_2Cl_2$, CuI, $Et_3N$, $CH_3CN$, 78° C., 16 h; (c) TFA, DCM, rt, 3 h; (d) $R_1$—Br, $K_2CO_3$, DMF, 110° C., 8 h.

-continued

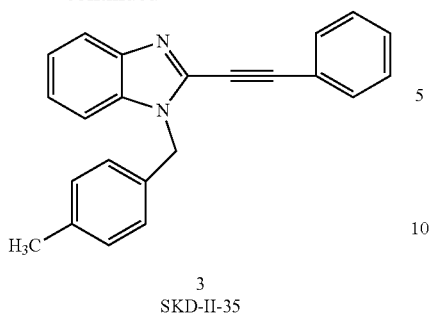

3
SKD-II-35

Reagents and conditions: (a) HCl, Ethylene glycol, 125-130° C.;
(b) 4-methylbenzyl chloride, K₂CO₃, DMF, 110° C.

Scheme 4

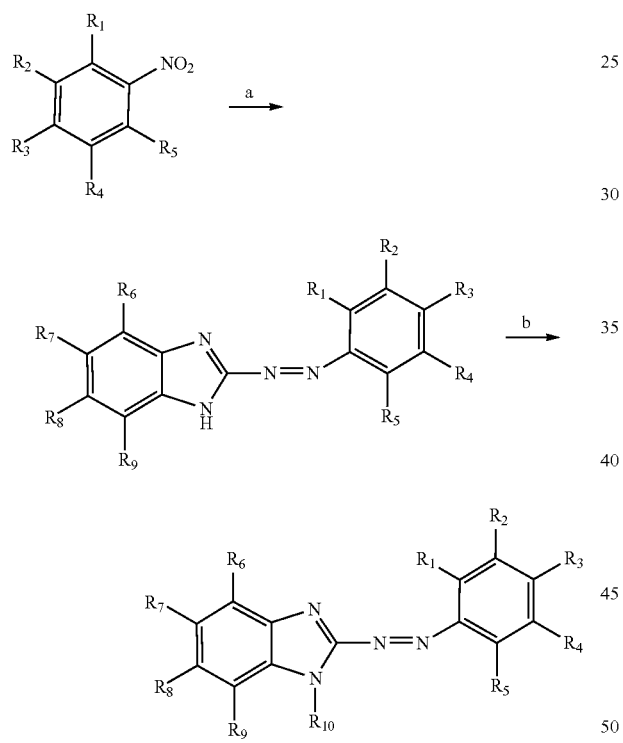

Reagents and conditions: (a), NaNO₂, HCl, 0° C., then Na₂CO₃, benzimidazole derivatives; (B) NaH, R₁₀—I, THF.

$R_1$, $R_2$, $R_3$, $R_4$, $R_5$, $R_6$, $R_7$, $R_8$, $R_9$ independently can be, for example, any of H; ($C_1$-$C_6$)alkyl, e.g., Me, Et; (($C_1$-$C_6$) alkoxy, e.g., OMe, OEt; or a halide. Rio can be, for example, ($C_1$-$C_6$)alkyl, e.g., Me, Et, n-propyl, and isopropyl; or ($C_3$-$C_{10}$)cycloalkyl, e.g., cyclopropane, cyclobutane, cyclopentane, and cyclohexane.

Examples 18-19 are structures of two exemplary compounds of Formula (II) and how they were prepared. The analytical data for the compounds thus prepared are also set forth in Examples 18-19 and the procedures for testing these compounds are described in Examples 20-22 that follow.

Example 1: Synthesis of (2S)-3-(4-chlorophenyl)-2-[(6-fluoronaphthalen-2-yl)-formamido-N-(3-phenyl-propyl)propanamide (CAP01687; Compound 4)

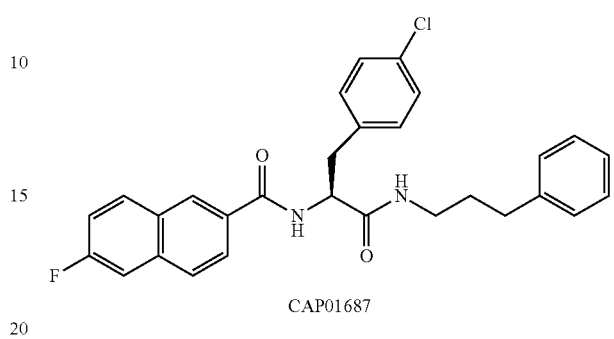

CAP01687

The scheme of synthesis shown below (Scheme 4) for making CAP01687 is exemplary of the synthesis of all of the compounds of Formula (I).

Scheme 4

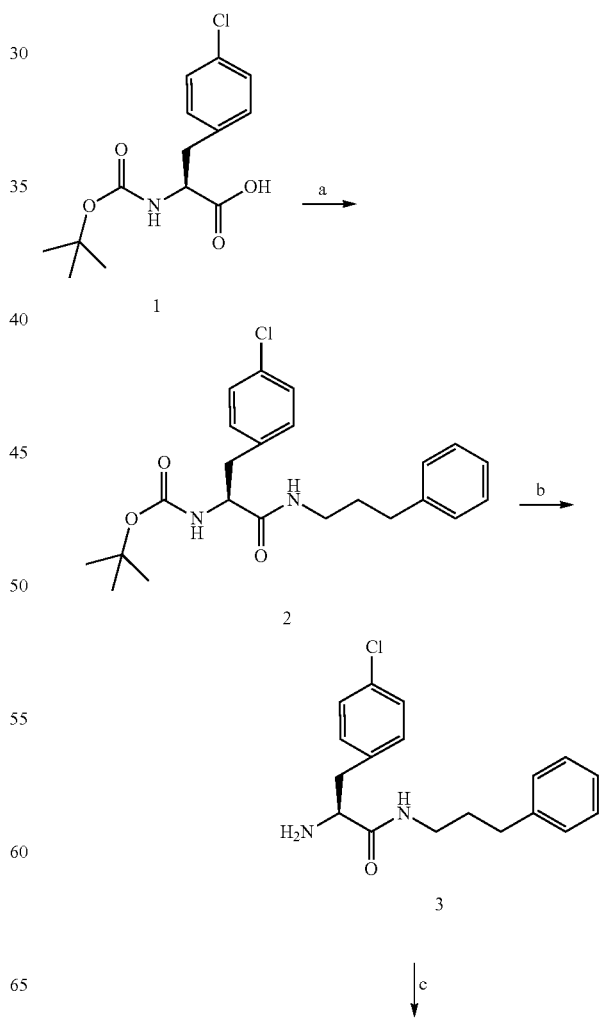

-continued

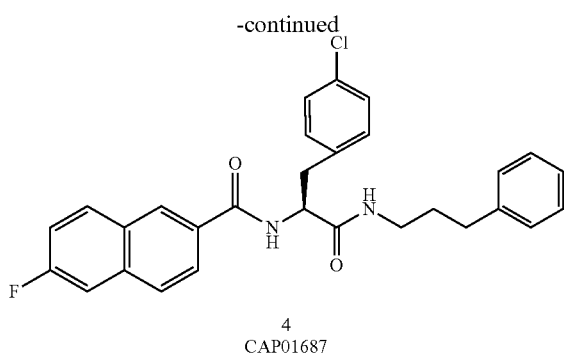

4
CAP01687

Synthesis of Intermediate Compound 2, tert-butyl N[(1S)-2(4-chlorophenyl)-1-[(3-phenyl)carbamoyl]ethyl]carbamate A mixture of Boc-L-4-chlorophenylalanine (923 mg, 3.08 mmol), 3-phenylpropylamine (417 mg, 3.08 mmol), 1-Ethyl-3-(3-dimethylaminopropyl)carbodiimide (EDC; 705 mg, 3.69 mmol), hydroxybenzotriazole (HOBt; 498 mg, 3.69 mmol), and N,N-Diisopropylethylamine (DIEA; 1.33 mL, 7.70 mmol) in DMF (15 mL) was stirred at room temperature for 16 h. The reaction mixture was partitioned between ethyl acetate and water. The organic layer was washed with saturated NaHCO$_3$ solution (100 ml×3), brine (100 ml×3), dried over MgSO$_4$ and filtered. The organic layer was concentrated on rotary evaporator and residue purified over silica gel column chromatography using hexanes-ethyl acetate to obtain compound 2 (960 mg, 75%). $^1$H NMR (500 MHz, DMSO-d$_6$) δ 1.30 (s, 9H), 1.62-1.67 (m, 2H), 2.51-2.54 (2H), 2.71-2.74 (m, 1H), 2.88-2.99 (m, 1H), 3.02-3.07 (m, 2H), 4.01-4.12 (m, 1H), 6.91 (d, J=9 Hz, 1H), 7.15-7.19 (m, 3H), 7.25-7.29 (m, 4H), 7.31 (d, J=8 Hz, 2H), 7.91 (t, J=5 Hz, 1H, NH); ESI-MS m/z 439 (M+Na)$^+$, 417 (M+H)$^+$.

Synthesis of Intermediate Compound 3, (2S)-2-amino-3(4-chlorophenyl)-N-(3-phenylpropyl)-propanamide (Compound 3)

A solution of compound 2 (48 mg, 0.11 mmol) in TFA (1 mL) and DCM (1 mL) was stirred at room temperature for 4 h. The solvents were removed in vacuo and dried under vacuum pump. This compound was used for the next step without further purification.

Synthesis of Final Compound 4

A mixture of compound 3 (36 mg, 0.11 mmol), 6-fluoro-2-naphthoic acid (22 mg, 0.11 mmol), EDC (26 mg, 0.13 mmol), HOBt (19 mg, 0.13 mmol), DIEA (0.1 mL, 0.57 mmol) in DMF (2 mL) was stirred at room temperature for 16 h. The reaction mixture was extracted with ethyl acetate (100 mL), washed with saturated NaHCO$_3$ solution (3×100 mL), brine (3×100 ml), dried (MgSO$_4$), and concentrated in vacuo. The residue was purified over silica gel column using hexane-ethyl acetate systems to afford compound 4 (37 mg, 70%). $^1$H NMR (500 MHz, DMSO-d$_6$) δ 1.66-1.72 (m, 2H), 2.53-2.57 (m, 2H), 3.01-3.14 (4H), 4.71-4.76 (m, 1H), 7.14-7.18 (m, 3H), 7.23-7.28 (m, 2H), 7.31 (d, J=8.5 Hz, 2H), 7.52 (d, J=8.5 Hz, 2H), 7.48-7.52 (m, 1H), 7.75-7.78 (m, 1H), 7.93-7.97 (m, 2H), 8.01-8.12 (m, 1H), 8.15 (t, J=5.5 Hz, 1H, NH), 8.47 (s, 1H), 8.74 (d, J=8.5 Hz, 1H); ESI-MS m/z 511 (M+Na)$^+$, 489 (M+H)$^+$.

Following the above mentioned procedure, other compounds were synthesized using the appropriate chemicals and reagents as shown in Scheme 4.

Example 2: (2S)-2-cyclohexyl-2-(naphthalen-1-yl-formamido)-N-(3-phenylpropyl)acetamide (CAP01678)

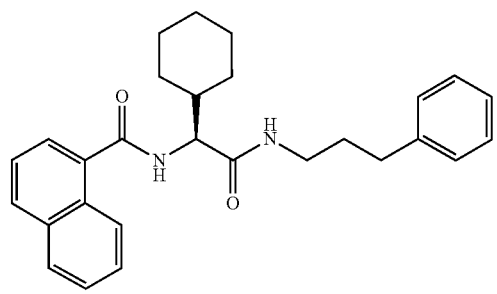

CAP01678

$^1$H NMR (500 MHz, DMSO-d6) δ 1.06-1.26 (m, 7H), 1.62-1.83 (m, 6H), 2.61 (t, J=5.6 Hz, 2H), 3.09-3.19 (m, 2H), 4.35-4.39 (m, 1H), 7.16-7.29 (m, 5H), 7.47-7.60 (m, 4H), 7.95 (d, J=8 Hz, 1H), 8.00 (d, J=8 Hz, 1H), 8.12 (t, J=5.6 Hz, 1H, NH), 8.16 (d, J=8.5 Hz, 1H), 8.45 (d, J=8 Hz, 1H); ESI-MS m/z 451 (M+Na)$^+$, 429 (M+H)$^+$.

Example 3: (2S)-2-(adamantan-1-yl)formamido-2-cyclohexyl-N-(3-phenylpropyl)acetamide (CAP01680)

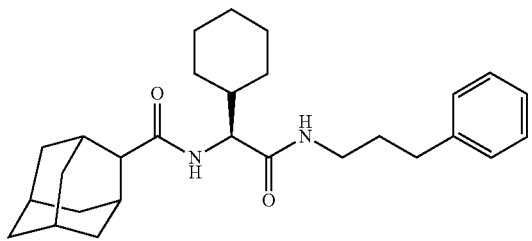

CAP01680

$^1$H NMR (500 MHz, DMSO-d6) δ 1.71-1.77 (m, 2H), 2.60 (t, J=6.5 Hz, 2H), 2.88-2.91 (m, 1H), 3.01-3.16 (m, 3H), 4.9-4.84 (m, 1H), 7.16-7.29 (m, 5H), 7.31-7.42 (m, 5H), 7.47-7.53 (m, 3H), 7.76 (d, J=8.5 Hz, 1H), 7.93 (d, J=9 Hz, 1H), 7.97 (d, J=8.7 Hz, 1H), 8.15 (t, J=5.6 Hz, 1H, NH), 8.70 (d, J=8.5 Hz, 1H); ESI-MS m/z 493 (M+Na)$^+$, 471 (M+H)$^+$.

Example 4: (2S)-3-(4-chlorophenyl)-2-(naphthalene-1-ylformamido)-N-(3-phenylpropyl)propanamide (CAP01681)

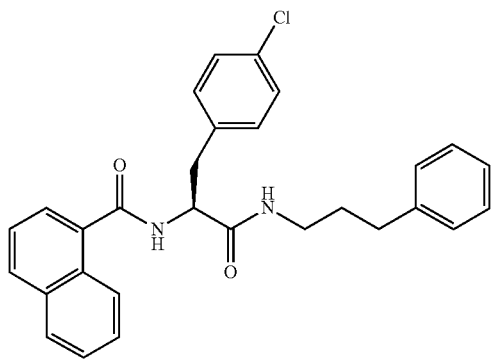

CAP01681

$^1$H NMR (500 MHz, DMSO-d6) δ 1.71-1.77 (m, 2H), 2.60 (t, J=6.5 Hz, 2H), 2.88-2.91 (m, 1H), 3.01-3.16 (m, 3H), 4.9-4.84 (m, 1H), 7.16-7.29 (m, 5H), 7.31-7.42 (m, 5H), 7.47-7.53 (m, 3H), 7.76 (d, J=8.5 Hz, 1H), 7.93 (d, J=9 Hz, 1H), 7.97 (d, J=8.7 Hz, 1H), 8.15 (t, J=5.6 Hz, 1H, NH), 8.70 (d, J=8.5 Hz, 1H); ESI-MS m/z 493 (M+Na)$^+$, 471 (M+H)$^+$.

Example 5: (2S)-3-(4-chlorophenyl)-2-(naphthalene-2-ylformamido)-N-(3-phenylpropyl)propanamide (CAP01684)

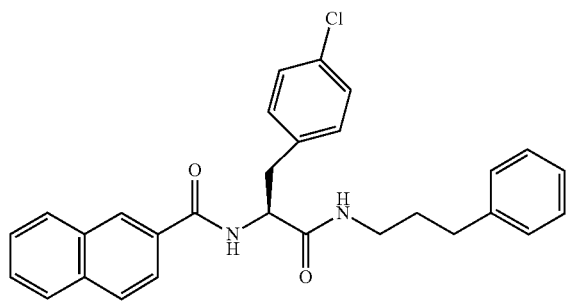

CAP01684

$^1$H NMR (500 MHz, DMSO-d6) δ 1.66-1.72 (2H), 2.54 (t, J=5.6 Hz, 2H), 3.01-3.14 (m, 4H), 4.71-4.76 (m, 1H), 7.14-7.19 (m, 3H), 7.23-7.28 (m, 2H), 7.32 (d, J=8.5 Hz, 2H), 7.38 (d, J=8.5 Hz, 2H), 7.57-7.62 (m, 2H), 7.88-8.01 (m, 4H), 8.15 (t, J=5.6 Hz, 1H, NH), 8.43 (d, J=1.1 Hz, 1H), 8.74 (d, J=5.6 Hz, 1H, NH); ESI-MS m/z 493 (M+Na)$^+$, 471 (M+H)$^+$.

Example 6: (2S)-2-(adamantan-1-ylformamido)-3-(4-chlorophenyl)-N-(3-phenylpropyl)propanamide (CAP01685)

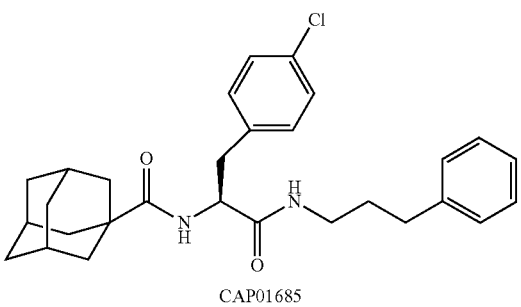 [SMILES: O=C(NCCCc1ccccc1)[C@H](Cc1ccc(Cl)cc1)NC(=O)C12CC3CC(CC(C3)C1)C2]

CAP01685

$^1$H NMR (500 MHz, DMSO-d6) δ 1.57-1.68 (m, 15H), 1.90-1.92 (m, 3H), 2.52 (t, J=6.2 Hz, 2H), 2.86-3.09 (m, 4H), 4.43-4.48 (m, 1H), 7.14-7.32 (m, 10H), 7.88 (t, J=5.7 Hz, 1H, NH); ESI-MS m/z 502 (M+Na)$^+$, 480 (M+H)$^+$.

Example 7: (2S)-3-(4-chlorophenyl)-N-(3-phenyl-propyl)-2-(quinolin-3-yl)formamidoprpanamide (CAP01686)

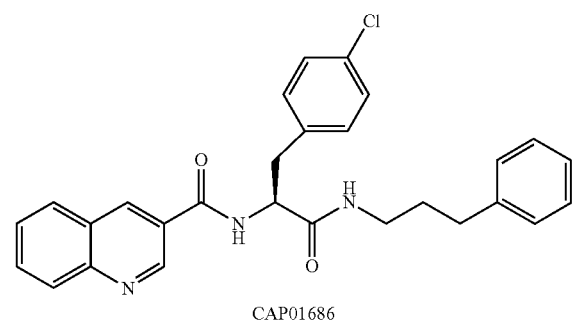 [SMILES: O=C(N[C@@H](Cc1ccc(Cl)cc1)C(=O)NCCCc1ccccc1)c1cnc2ccccc2c1]

CAP01686

$^1$H NMR (500 MHz, DMSO-d6) δ 1.66-1.71 (m, 2H), 2.54 (t, J=6.5 Hz, 2H), 2.98-3.14 (m, 4H), 4.72-4.78 (m, 1H), 7.14-7.39 (m, 9H), 7.69 (t, J=7.5 Hz, 1H), 7.86 (t, J=7.5 Hz, 1H), 8.08 (t, J=7.6 Hz, 2H), 8.19 (t, J=6.3 Hz, 1H, NH), 8.80 (s, 1H), 9.00 (d, J=6.2 Hz, 1H, NH), 9.21 (s, 1H); ESI-MS m/z 494 (M+Na)$^+$, 472 (M+H)$^+$.

Example 8: (2S)-3-(4-chlorophenyl)-2-(1H-indazol-6-ylformamido)-N-(3-phenylpropyl)propanamide (CAP01688)

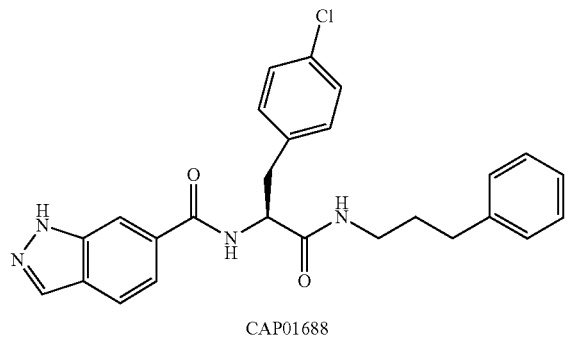 [SMILES: O=C(N[C@@H](Cc1ccc(Cl)cc1)C(=O)NCCCc1ccccc1)c1ccc2cn[nH]c2c1]

CAP01688

¹H NMR (500 MHz, DMSO-d6) δ 1.66-1.72 (m, 2H), 2.55 (t, J=7 Hz, 2H), 3.00-3.12 (m, 4H), 4.67-4.72 (m, 1H), 7.14-7.19 (m, 3H), 7.24-7.28 (m, 2H), 7.31 (d, J=8 Hz, 2H), 7.37 (d, J=8 Hz, 2H), 7.54 (d, J=8.5 Hz, 1H), 7.79 (d, J=7.8 Hz, 1H), 8.03 (s, 1H), 8.12-8.14 (m, 2H), 8.69 (d, J=8 Hz, 1H), 13.35 (br s, 1H, NH); ESI-MS m/z 483 (M+Na)$^+$, 461 (M+H)$^+$.

Example 9: (2S)-3-(4-chlorophenyl)-2-[(6-fluoronaphthalen-2-yl)-formamido]-N-[3-(pyridine-3-yl)propyl]propanamide (CAP01693)

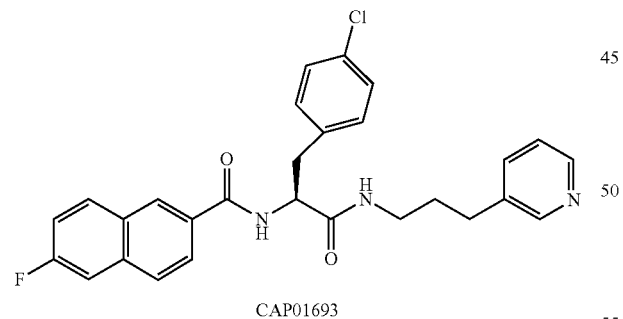

CAP01693

¹H NMR (500 MHz, DMSO-d6) δ 1.68-1.71 (m, 2H), 2.55 (t, J=5.6 Hz, 2H), 3.01-3.14 (m, 4H), 4.70-4.74 (m, 1H), 7.31-7.38 (m, 5H), 7.50 (t, J=8 Hz, 1H), 7.61 (d, J=8 Hz, 1H), 7.76 (d, J=8 Hz, 1H), 7.92-7.98 (m, 2H), 8.11 (t, J=8 Hz, 1H), 8.18 (t, J=5.4 Hz, 1H, NH), 8.40-8.48 (m, 3H), 8.75 (d, J=8 Hz, 1H); ESI-MS m/z 512 (M+Na)$^+$, 490 (M+H)$^+$.

Example 10: (2S)-3-(4-chlorophenyl)-2-[(3-phenyl-1H-indazol-6yl)formamido]-N-(3-phenylpropyl)propanamide (CAP01717)

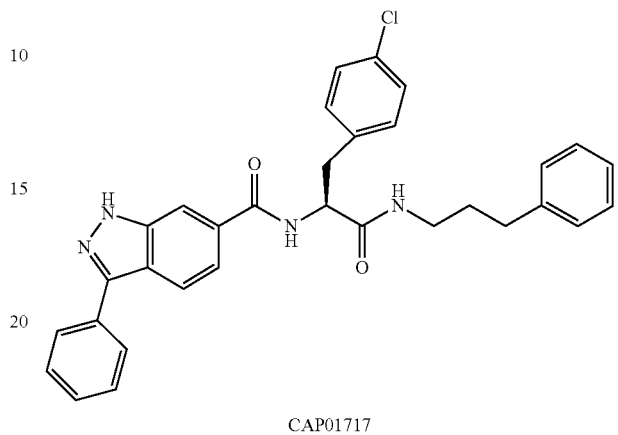

CAP01717

¹H NMR (500 MHz, DMSO-d6) δ 1.67-1.73 (m, 2H), 2.55 (t, J=5.6 Hz, 2H), 3.02-3.14 (m, 4H), 4.69-4.74 (m, 1H), 7.15-7.19 (m, 3H), 7.25-7.32 (m, 4H), 7.38-7.43 (m, 3H), 7.53 (t, J=8 Hz, 2H), 7.65 (dd, J=8 and 1.2 Hz, 1H), 8.00 (d, J=7 Hz, 2H), 8.07-8.11 (m, 2H), 8.16 (t, J=5.6 Hz, 1H, NH), 8.78 (d, J=8.5 Hz, 1H), 13.54 (br s, 1H, NH); ESI-MS m/z 560 (M+Na)$^+$, 538 (M+H)$^+$.

Example 11: (2S)-2-(1H-1,3-benzodiazol-2-ylformamido)-3-(4-chlorophenyl)-N-(3-phenylpropyl)propanamide (CAP01721)

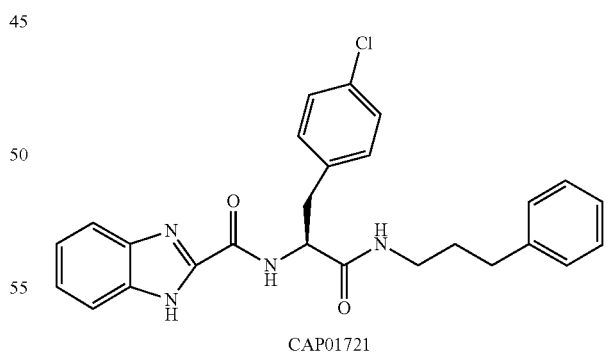

CAP01721

¹H NMR (500 MHz, DMSO-d6) δ 1.67-1.72 (m, 2H), 2.55 (t, J=5.4 Hz, 2H), 3.02-3.14 (m, 4H), 4.71-4.75 (m, 1H), 7.14-7.19 (m, 3H), 7.24-7.34 (m, 8H), 7.50 (d, J=8 Hz, !H), 7.74 (d, J=8 Hz, 1H), 8.19 (t, J=5.6 Hz, 1H, NH), 8.68 (d, J=8.5 Hz, 1H, NH), 13.20 (br s, 1H, NH); ESI-MS m/z 483 (M+Na)$^+$, 461 (M+H)$^+$.

Example 12: (2S)-3-(4-chlorophenyl)-2-(1H-indazol-3ylformamido)-N-(3-phenylpropyl)propanamide (CAP01722)

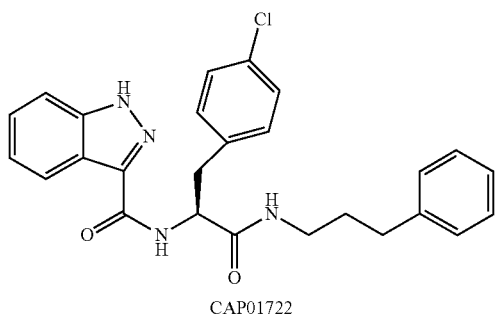 [SMILES: O=C(N[C@@H](Cc1ccc(Cl)cc1)C(=O)NCCCc1ccccc1)c1n[nH]c2ccccc12]

CAP01722

¹H NMR (500 MHz, DMSO-d6) δ 1.65-1.71 (m, 2H), 2.54 (t, J=5.6 Hz, 2H), 3.01-3.12 (m, 4H), 4.73-4.78 (m, 1H), 7.11-7.29 (m, 10H), 7.41 (t, J=8 Hz, 1H), 7.61 (d, J=7.6 Hz, 1H), 8.01-8.14 (m, 2H), 8.20 (t, J=5.4 Hz, 1H, NH), 13.66 (br s, 1H, NH); ESI-MS m/z 483 (M+Na)⁺, 461 (M+H)⁺.

Example 13: (2S)-2-[(6-fluoronaphthalen-2-yl)formamido]-2-phenyl-N-(3-phenylpropyl)acetamide (CAP01723)

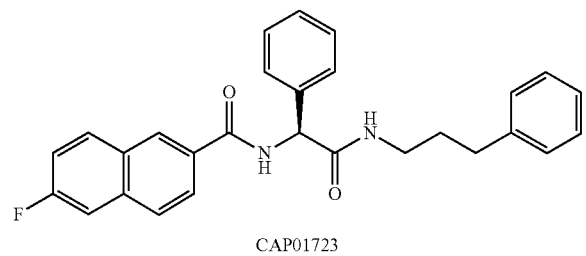 [SMILES: O=C(N[C@H](C(=O)NCCCc1ccccc1)c1ccccc1)c1ccc2cc(F)ccc2c1]

CAP01723

¹H NMR (500 MHz, DMSO-d6) δ 1.65-1.71 (m, 2H), 2.47-2.51 (m, 2H), 3.08-3.14 (m, 2H), 5.73 (d, J=7 Hz, 1H), 7.10-7.25 (m, 3H), 7.31-7.57 (m, 8H), 7.78 (dd, J=8 and 1.4 Hz, 1H), 7.96=8.03 (m, 2H), 8.12-8.15 (m, 1H), 8.37 (t, J=5.6 Hz, 1H, NH), 8.62 (s, 1H), 8.92 (d, J=8 Hz, 1H); ESI-MS m/z 463 (M+Na)⁺, 441 (M+H)⁺.

Example 14: (2S)-2-(4-chlorophenyl)-2-[(6-fluoronaphthalen-2-yl)formamido]-N-[3-(pyridine-3-yl)propyl]acetamide (SKD-II-13)

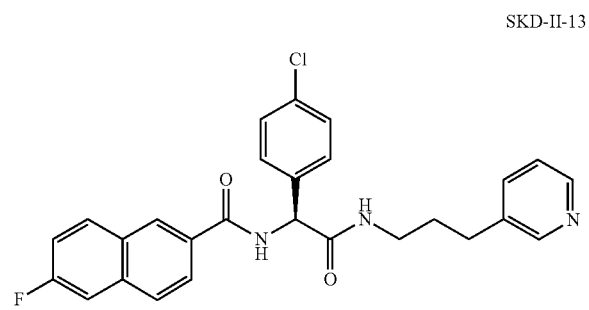 [SMILES: O=C(N[C@H](C(=O)NCCCc1cccnc1)c1ccc(Cl)cc1)c1ccc2cc(F)ccc2c1]

SKD-II-13

¹H NMR (500 MHz, DMSO-d6) δ 1.68-1.72 (m, 2H), 2.52-2.54 (m, 2H), 3.10-3.12 (m, 2H), 5.74 (d, J=7 Hz, 1H), 7.27-7.28 (m, 1H), 7.44-7.60 (m, 6H), 7.78 (d, J=5 Hz, 1H), 7.96-8.03 (m, 2H), 8.11-8.14 (m, 1H), 8.42-8.44 (m, 2H), 8.62 (s, 1H), 9.01 (d, J=8 Hz, 1H); ESI-MS m/z 498 (M+Na)⁺, 476 (M+H)⁺.

Example 15: $K_i$ Estimation

Ligand binding was measured by fluorescence polarization of a fluorescein isothiocyanate (FITC) labeled probe (as described by Bollini, et al 2002) in conjunction with recombinant full-length FKBP12 and FKBP52. Binding saturation experiments were performed to determine the probe $K_d$ for FKBP12 or FKBP52 using GraphPad software. Ligand displacement from FKBP12 or FKBP52 was measured by fluorescence polarization in the presence of various compound concentrations. $IC_{50}$ for each compound was determined using GraphPad software. The $IC_{50}$ value for each compound was used to estimate the $K_i$ using the equations described by Nikolovska-Coleska, et al 2004. See Table 1 below.

TABLE 1

| ID | Structure | FKBP12 Ki (μM) | FKBP52 Ki (μM) |
|---|---|---|---|
| CAP01564 | 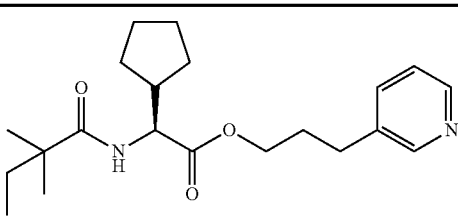 | >25 | >25 |
| | 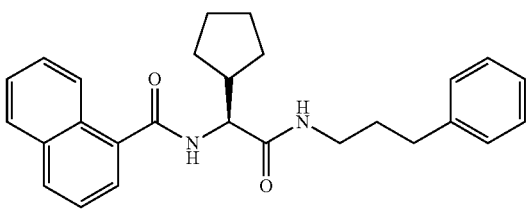 [SMILES: O=C(N[C@H](C(=O)NCCCc1ccccc1)C1CCCC1)c1cccc2ccccc12] | 10.30 | 12.12 |

TABLE 1-continued

| ID | Structure | FKBP12 Ki (μM) | FKBP52 Ki (μM) |
|---|---|---|---|
| CAP01678 | 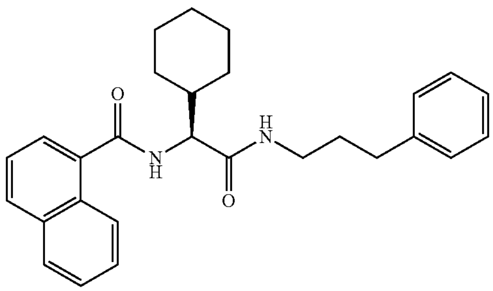 [SMILES: O=C(N[C@H](C(=O)NCCCc1ccccc1)C1CCCCC1)c1cccc2ccccc12] | 2.70 | 13.20 |
| CAP01680 | 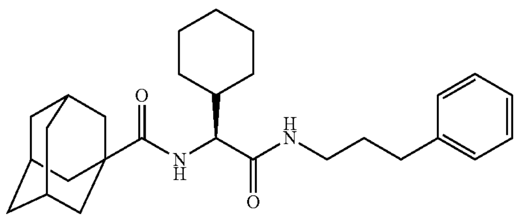 [SMILES: O=C(NCCCc1ccccc1)[C@@H](NC(=O)C12CC3CC(CC(C3)C1)C2)C1CCCCC1] | 35.40 | 72.10 |
| CAP01681 | 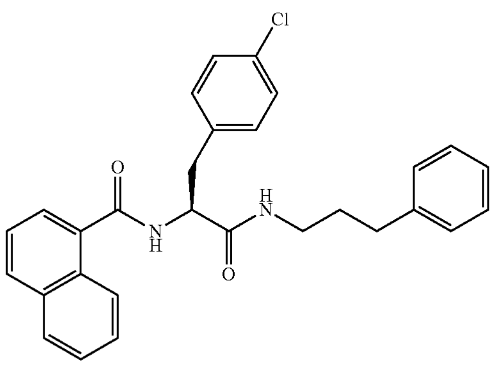 [SMILES: O=C(N[C@@H](Cc1ccc(Cl)cc1)C(=O)NCCCc1ccccc1)c1cccc2ccccc12] | 1.62 | 1.88 |
| CAP01684 | 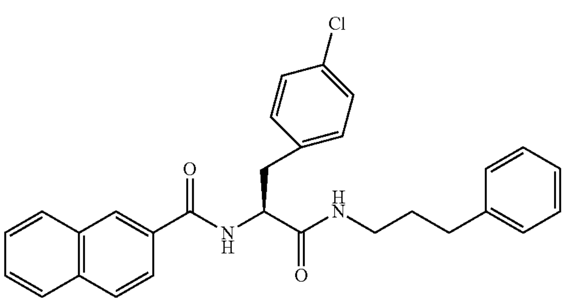 [SMILES: O=C(N[C@@H](Cc1ccc(Cl)cc1)C(=O)NCCCc1ccccc1)c1ccc2ccccc2c1] | 2.39 | 1.66 |
| CAP01685 | 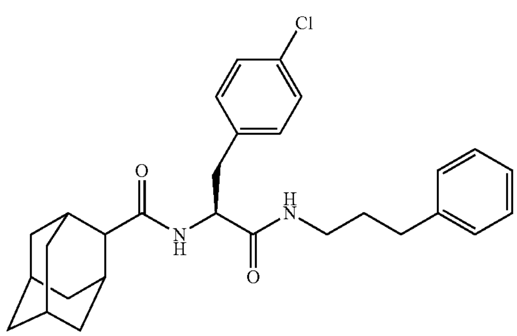 [SMILES: O=C(N[C@@H](Cc1ccc(Cl)cc1)C(=O)NCCCc1ccccc1)C1C2CC3CC(C2)CC1C3] | 32.50 | 2.70 |

TABLE 1-continued

| ID | Structure | FKBP12 Ki (μM) | FKBP52 Ki (μM) |
|---|---|---|---|
| CAP01686 | 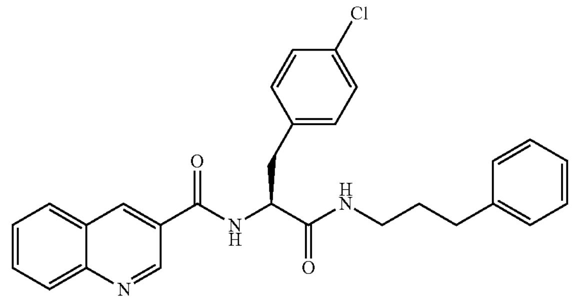 [SMILES: O=C(N[C@@H](Cc1ccc(Cl)cc1)C(=O)NCCCc1ccccc1)c1cnc2ccccc2c1] | 3.17 | 6.28 |
| CAP01687 | 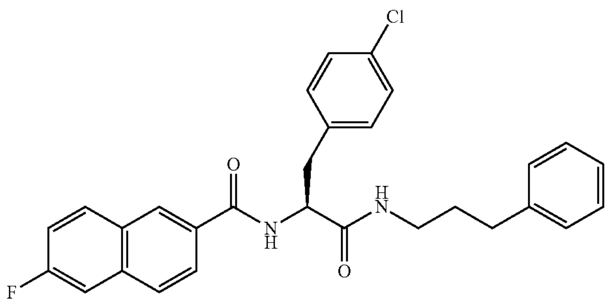 [SMILES: O=C(N[C@@H](Cc1ccc(Cl)cc1)C(=O)NCCCc1ccccc1)c1ccc2cc(F)ccc2c1] | 0.58 | 3.37 |
| CAP01688 | 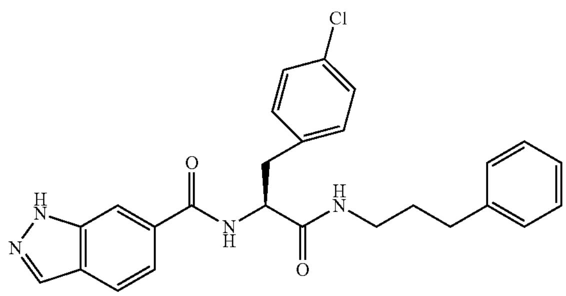 [SMILES: O=C(N[C@@H](Cc1ccc(Cl)cc1)C(=O)NCCCc1ccccc1)c1ccc2cn[nH]c2c1] | 3.19 | 6.81 |
| CAP01689 | 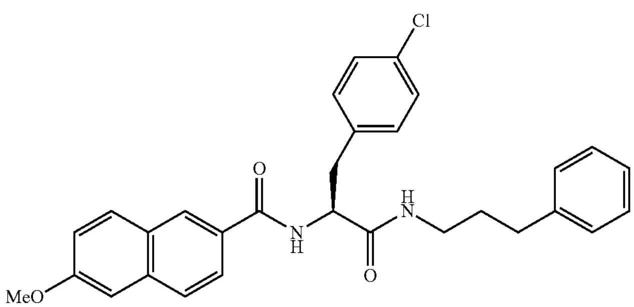 [SMILES: COc1ccc2cc(C(=O)N[C@@H](Cc3ccc(Cl)cc3)C(=O)NCCCc3ccccc3)ccc2c1] | 1.16 | 9.32 |
| CAP01690 | 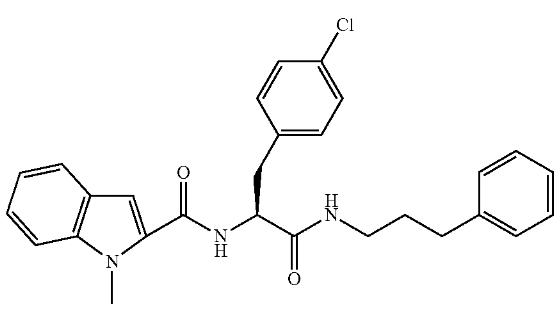 [SMILES: Cn1c(C(=O)N[C@@H](Cc2ccc(Cl)cc2)C(=O)NCCCc2ccccc2)cc2ccccc21] | 4.44 | 11.98 |

TABLE 1-continued
| ID | Structure | FKBP12 Ki (μM) | FKBP52 Ki (μM) |
|---|---|---|---|
| CAP01740 | 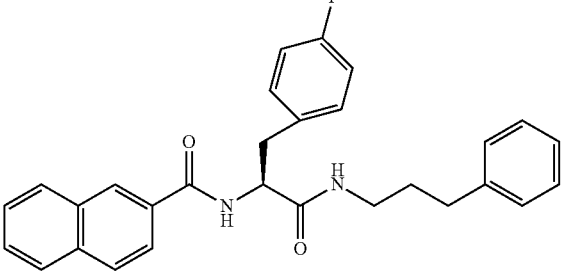 | >40 | >40 |
| CAP01691 | 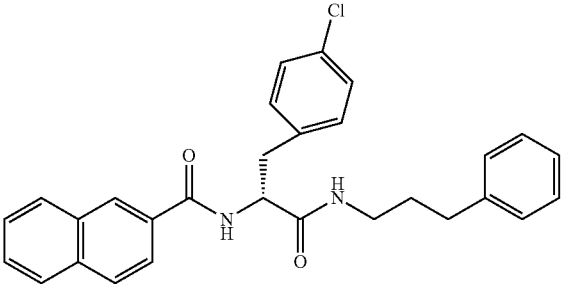 D-isomer | >50 | >50 |
| CAP01692 | 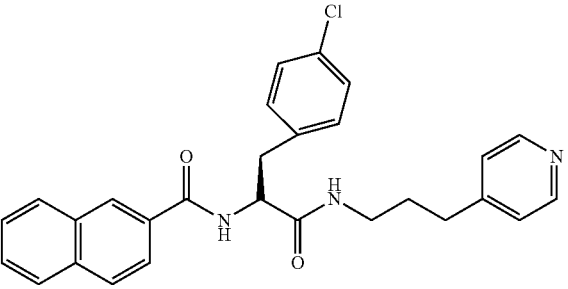 | 2.38 | 26.17 |
| CAP01693 | 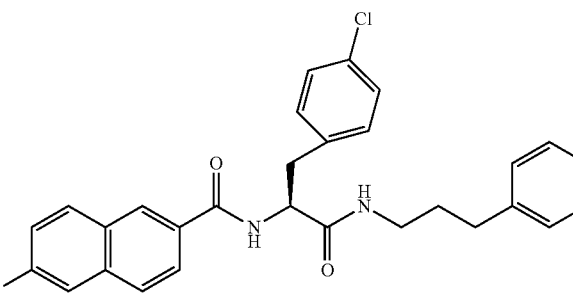 | 0.19 | 2.49 |
| CAP01694 | 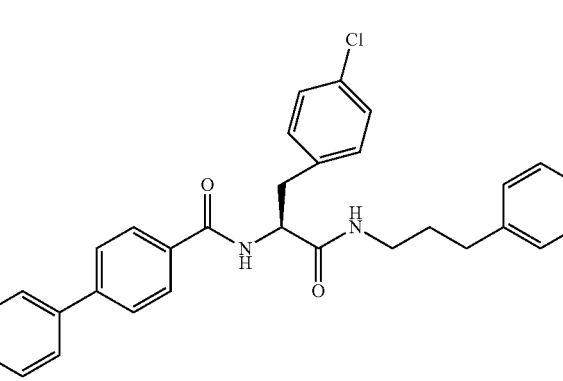 | 79% at 20 μM | 61% at μM |

TABLE 1-continued

| ID | Structure | FKBP12 Ki (μM) | FKBP52 Ki (μM) |
|---|---|---|---|
| CAP01717 | 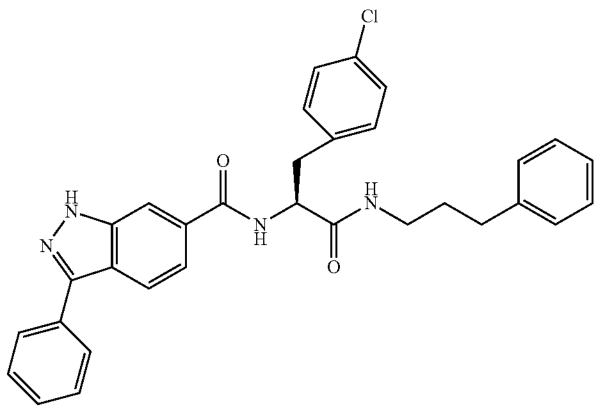 [SMILES: O=C(N[C@@H](Cc1ccc(Cl)cc1)C(=O)NCCCc1ccccc1)c1ccc2c(-c3ccccc3)n[nH]c2c1] | 1.12 | 4.04 |
| CAP01719 | 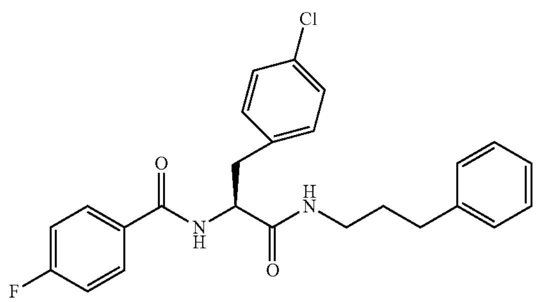 [SMILES: O=C(N[C@@H](Cc1ccc(Cl)cc1)C(=O)NCCCc1ccccc1)c1ccc(F)cc1] | >25 | >25 |
| CAP01720 | 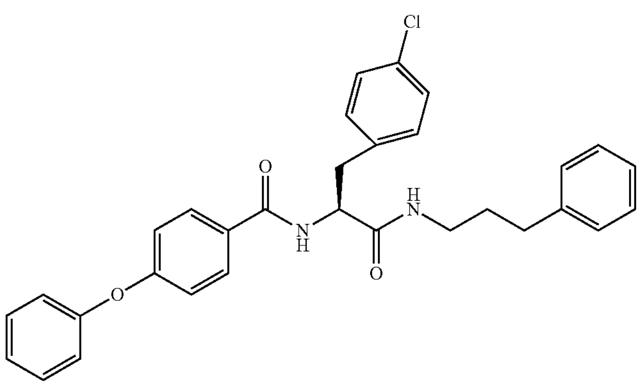 [SMILES: O=C(N[C@@H](Cc1ccc(Cl)cc1)C(=O)NCCCc1ccccc1)c1ccc(Oc2ccccc2)cc1] | 6.55 | 6.34 |
| CAP01721 | 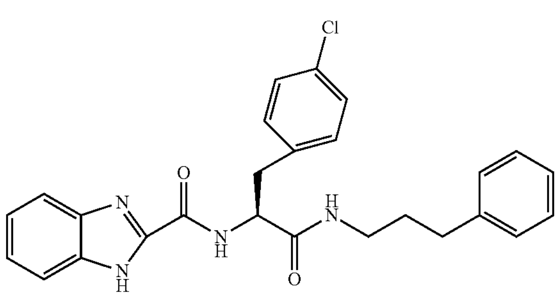 [SMILES: O=C(N[C@@H](Cc1ccc(Cl)cc1)C(=O)NCCCc1ccccc1)c1nc2ccccc2[nH]1] | 0.95 | >50 |

TABLE 1-continued

| ID | Structure | FKBP12 Ki (μM) | FKBP52 Ki (μM) |
|---|---|---|---|
| CAP01722 | 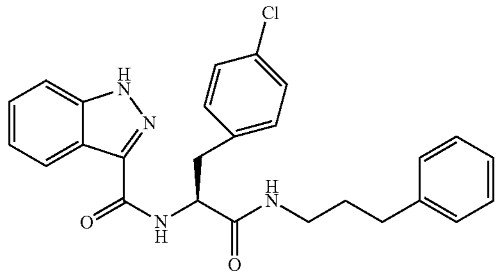 [SMILES: O=C(N[C@@H](Cc1ccc(Cl)cc1)C(=O)NCCCc1ccccc1)c1n[nH]c2ccccc12] | 35% at 10 μM | ND |
| CAP01723 | 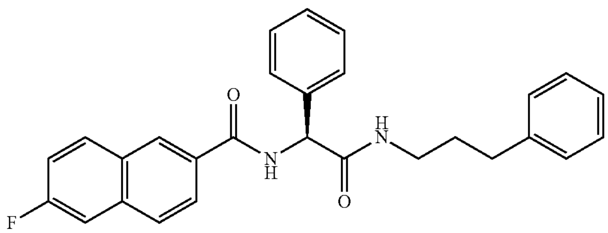 [SMILES: O=C(N[C@H](C(=O)NCCCc1ccccc1)c1ccccc1)c1ccc2cc(F)ccc2c1] | 0.23 | 0.069 |
| SKD-II-13 | 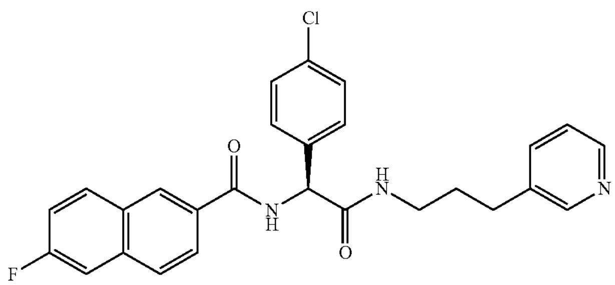 [SMILES: O=C(N[C@H](C(=O)NCCCc1cccnc1)c1ccc(Cl)cc1)c1ccc2cc(F)ccc2c1] | ND | ND |
| SKD-II-11 | 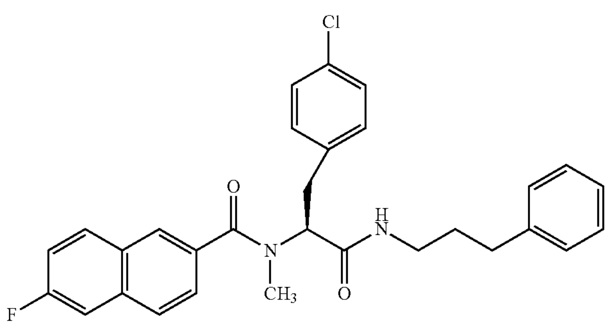 [SMILES: CN(C(=O)c1ccc2cc(F)ccc2c1)[C@@H](Cc1ccc(Cl)cc1)C(=O)NCCCc1ccccc1] | ND | ND |
| SKD-I-156 | 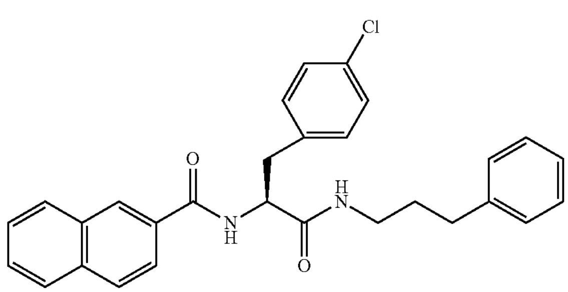 [SMILES: O=C(N[C@@H](Cc1ccc(Cl)cc1)C(=O)NCCCc1ccccc1)c1ccc2ccccc2c1] | ND | ND |

Example 16: Neuroprotection

BE(2)-M17 human neuroblastoma cells engineered to stably express either wild type or A53T mutant α-synuclein, PC12 rat pheochromocytoma, or SH-SY5Y human neuroblastoma cells were cultured in 96-well cell culture dishes in a humidified incubator at 37° C., 5% $CO_2$. The growth medium was supplemented with 0.1% dimethyl sulfoxide (vehicle control) or compounds dissolved in dimethyl sulfoxide. Following 2 hours of exposure to compounds, the growth medium was further supplemented with 6-hydroxydopamine (or 0.1% ascorbic acid vehicle control) and incubated for an additional 24-48 hours.

Figure 1B:
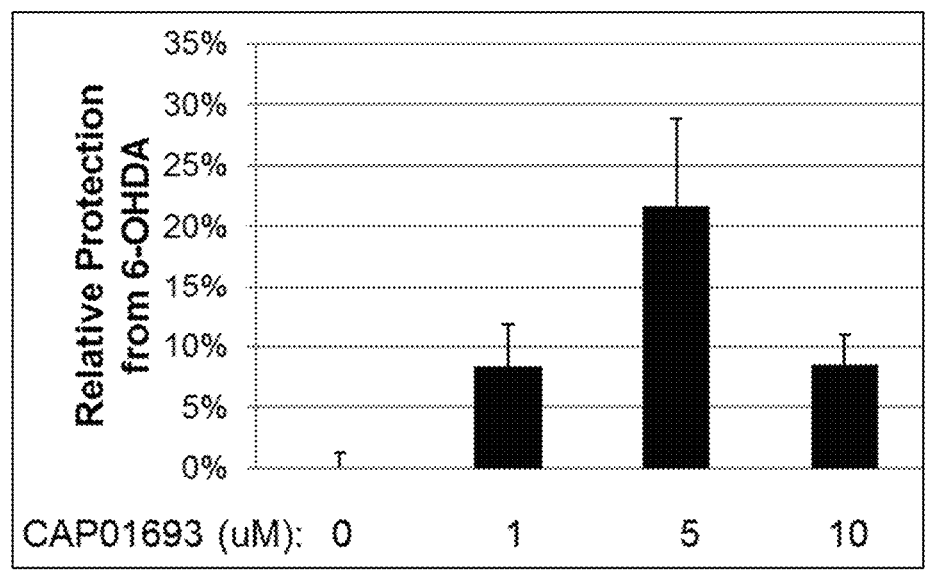
Figure 2:
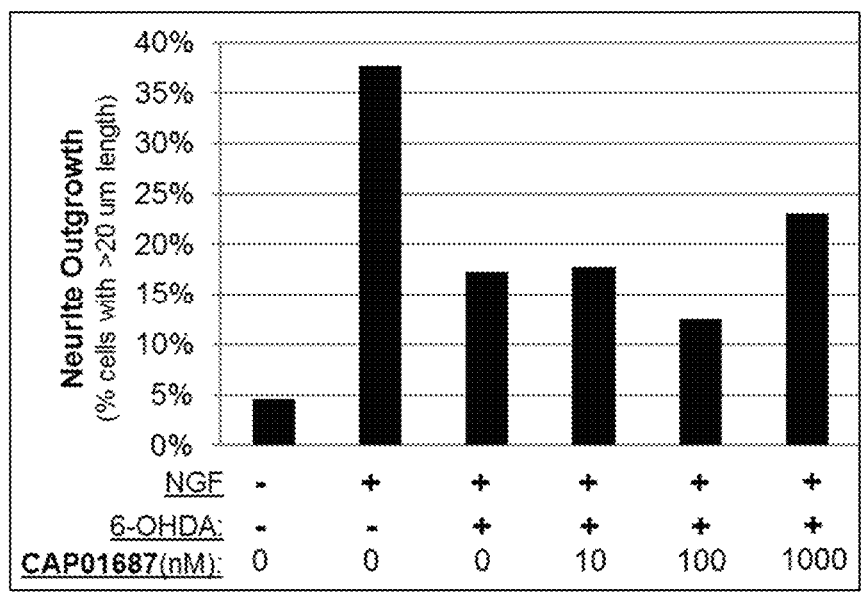
FIG. 2 is a bar graph showing promotion of neurite outgrowth by dual acting FKBP12 and FKBP52 inhibitory exemplary compound CAP01687.
Figure 3A:
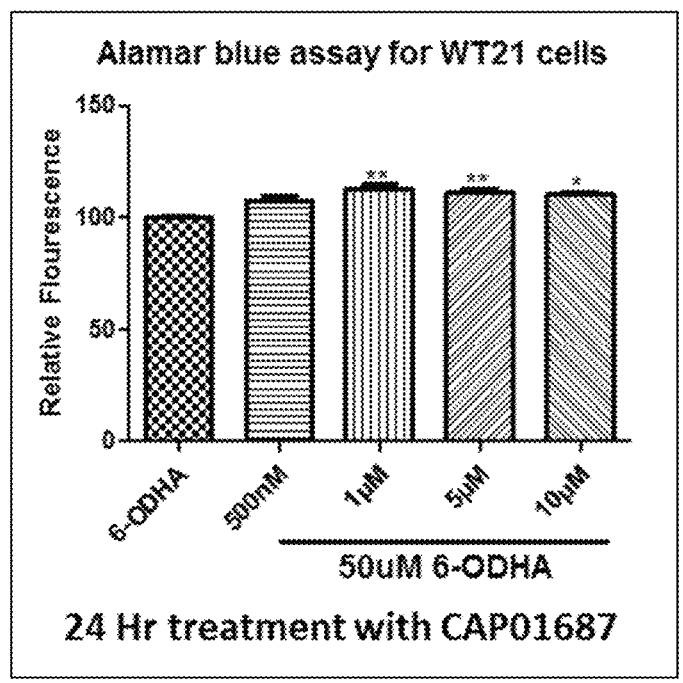
FIG. 3A is a bar graph showing neuroprotection resulting from the administration of dual acting FKBP12 and FKBP52 inhibitory exemplary compound CAP01687 to wild type α-synuclein overexpressing BE(2)-M17 cells, as measured by Alamar Blue assay.
Figure 3B:
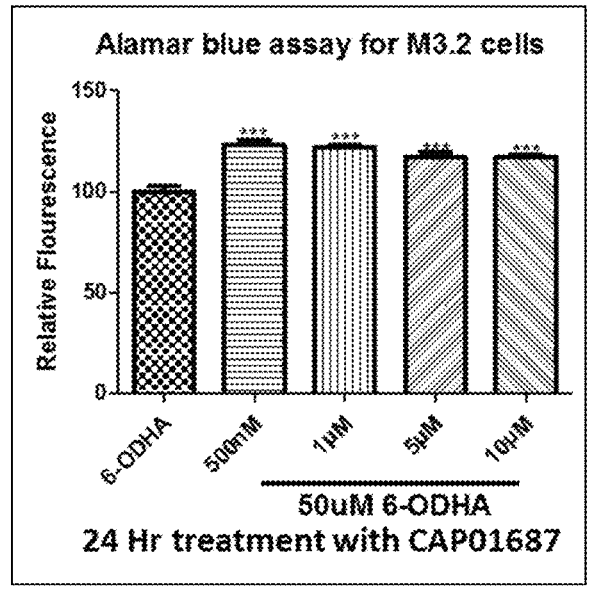
FIG. 3B is a bar graph showing neuroprotection resulting from the administration of dual acting FKBP12 and FKBP52 inhibitory exemplary compound CAP01687 to A53T mutant α-synuclein overexpressing BE(2)-M17 cells (M3.2), also as measured by Alamar Blue assay.

Cell viability was measured by reduction of WST-8 or AlamarBlue® and the relative protection from 6-hydroxydopamine was measured by calculating the percentage of viable cells normalized to 6-hydroxydopamine treated cells in the absence of compound. See FIGS. 1A and 1B for neuroprotection observed in PC12 cells treated with dual acting FKBP12 and FKBP52 inhibitory exemplary compounds CAP01687 (FIG. 1A) and CAP01693 (FIG. 1B) measured using WST-8 assay. Specifically, FIGS. 1A and 1B, show relative percent protection from 6-OHDA, the vehicle control being set to 0% relative protection. Also see FIG. 3A for a demonstration of neuroprotection in wild type α-synuclein overexpressing BE(2)-M17 cells, resulting from treating the cells with dual acting FKBP12 and FKBP52 inhibitory exemplary compound CAP01687, as measured by Alamar Blue assay. Neuroprotection was also observed in A53T mutant α-synuclein overexpressing BE(2)-M17 cells (M3.2) treated with CAP01687 (FIG. 3B). The bars in FIGS. 3A and 3B depict relative percent fluorescence, which is proportional to cell viability, with the vehicle control being 100%.]

Example 17: Neurite Outgrowth

PC12 rat pheochromocytoma or SH-SY5Y human neuroblastoma cells were grown on glass coverslips in a 24-well cell culture dish in a humidified incubator at 37° C., 5% $CO_2$. After 24 hours, the cells were washed with phosphate buffered saline and the serum concentration of the growth medium was reduced to 0.2%. After 16 hours in the reduced serum medium, 0.1% dimethyl sulfoxide (vehicle control) or compounds dissolved in dimethyl sulfoxide were added to the growth medium. Following 2 hours of exposure to compounds, the growth medium was supplemented with 6-hydroxydopamine (or 0.1% ascorbic acid vehicle control), nerve growth factor (or phosphate-buffered saline vehicle control), in addition to 0.1% dimethyl sulfoxide (vehicle control) or compounds dissolved in dimethyl sulfoxide. After 24 hours incubation the medium was removed and replaced with ice-cold methanol and cells were incubated for 10 minutes at −20° C. The cells were washed twice with phosphate-buffered saline and mounted on slides for light microscopy. Phase contrast images were captured at 20× magnification and the percentage of cells with neurites longer than 20 μm were scored for approximately 200 cells in each condition using ImageJ software. See FIGS. 3A and 3B for promotion of neurite outgrowth by dual acting FKBP12 and FKBP52 inhibitory exemplary compound CAP01687.

Example 18. Preparation of 2-[2-(4-fluorophenyl) vinyl]-1-(4-methylbenzyl)-1H-benzimidazole (CAP01551)

Preparation of 2-[2-(4-fluorophenyl)vinyl-1H-benzimidazole (1) (Scheme 1)

1,2-Phenylendiamine 4.32 g (40 mmol) and conc. HCl (30 mL) were added to a solution of 4-fluorocinnamic acid 4.98 g (30 mmol) in ethylene glycol (40 mL). The mixture was heated to 125-135° C. for 4 h. The reaction was allowed to cool to room temperature, diluted with water and made basic with conc. $NH_4OH$. The resulting precipitate was collected by filtration and recrystallized from ethanol/water. Yield: 6.22 g (87%).

Preparation of 2-[2-(4-fluorophenyl)vinyl]-1-(4-methylbenzyl)-1H-benzimidazole (CAP01551)

2-[2-(4-fluorophenyl)vinyl-1H-benzimidazole (4.77 g, 20 mmol) were treated with 4-methylbenzyl chloride (3.10 g, 22 mmol) in the presence of 3.45 g (25 mmol) anhydrous $K_2CO_3$ in DMF (100 ml). The mixture was heated to 110° C. and stirred for 6 h. Solvent was removed by evaporation, crude product was washed with water and recrystallized from hexane. Yield 4.65 g (68%) as white crystals). $^1$H NMR (500 MHz, DMSO-$d_6$) δ 2.25 (s, 3H), 5.21 (s, 2H), 7.02-7.38 (m, 8H), 7.50-7.64 (m, 3H), 7.81-7.89 (m, 3H); ESI-MS: m/z 343 (M+H)$^+$.

Example 19: Preparation of 1-[(4-methylphenyl) methyl]-2-(2-phenylethynyl)-1H-1,3-benzodiazole (3, SKD-II-35)

Synthesis of 2-(2-phenylethynyl)-1H-1,2-benzodiazole (2)

This compound was synthesized using scheme 3.

A mixture 1,2-phenylendiamine (1.15 g, 10.06 mmol), phenylpropiolic acid (1.10 g, 7.56 mmol), conc. HCl (8 ml) in ethylene glycol (10 mL) was stirred at 130° C. for 6 h. The reaction mixture was allowed to cool to room temperature, diluted with water, and made basic with conc. NH4OH. The reaction mixture was extracted with ethyl acetate, dried over $MgSO_4$, and concentrated in vacuo. The residue was purified over silica gel column using hexane-ethyl acetate system to give compound 2 (60%)). $^1$H NMR (500 MHz, DMSO-$d_6$) δ 7.23-7.25 (m, 2H), 7.48-7.54 (m, 3H), 7.62-7.64 (m, 2H), 7.84-7.86 (m, 2H), 12.43 (br s, 1H, NH).

Synthesis of 1-[(4-methylphenyl)methyl]-2-(2-phenylethynyl)-1H-1,3-benzodiazole (3, SKD-II-35)

A mixture of 2 (64 mg. 0.29 mmol), 4-methylbenzyl chloride (45 mg, 0.31 mmol), K2CO3 (52 mg, 0.37 mmol) in DMF (2 mL) was stirred at 110° C. for 6 h. The reaction mixture was cooled down to room temperature, and water was added, extracted with ethyl acetate, washed with brine (6×50 ml), dried ($MgSO_4$). The residue was recrystallized from hexane. Yield: 75%. $^1$H NMR (500 MHz, DMSO-$d_6$) δ 2.23 (s, 3H, CH3), 5.62 (s, 2H), 7.14 (d, J=8.2 Hz, 2H), 7.22 (d, J=8.2 Hz, 2H), 7.27-7.32 (m, 2H), 7.50-7.53 (m, 3H), 7.62-7.70 (m, 4H), ESI-MS: m/z 345 (M+Na)$^+$, 323 (M+H)$^+$.

Example 20. $K_i$ Estimation

Ligand binding was measured by fluorescence polarization of a fluorescein isothiocyanate (FITC) labeled probe (as described by Bollini, et al 2002) in conjunction with recombinant full-length FKBP12 and FKBP52. Binding saturation experiments were performed to determine the probe $K_d$ for FKBP12 or FKBP52 using GraphPad software. Ligand displacement from FKBP12 or FKBP52 was measured by fluorescence polarization in the presence of various compound concentrations and the $IC_{50}$ for each compound was determined using GraphPad software. The $IC_{50}$ values for each compound were used to estimate the $K_i$ using the equations described by Nikolovska-Coleska, et al 2004. The $IC_{50}$ value for each compound was used to estimate the $K_i$ using the equations described by Nikolovska-Coleska, et al 2004. See Tables 2 and 3 below.

TABLE 2
| ID | Structure | FKBP12 Ki (μM) or % | FKBP52 Ki (μM) or % |
|---|---|---|---|
| CAP01509 | 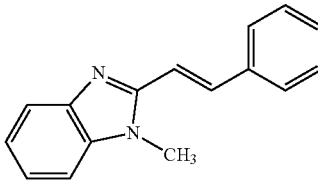 | >10 | >10 |
| CAP01510 | 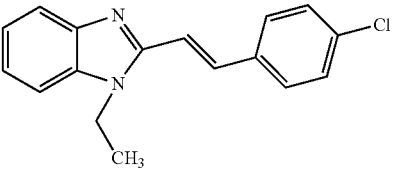 [SMILES: CCn1c(/C=C/c2ccc(Cl)cc2)nc2ccccc21] | 2.90 | 9.54 |
| CAP01540 | 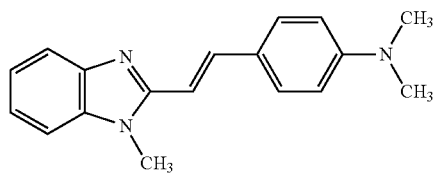 [SMILES: CN(C)c1ccc(/C=C/c2nc3ccccc3n2C)cc1] | 2.20 | 5.50 |
| CAP01547 | 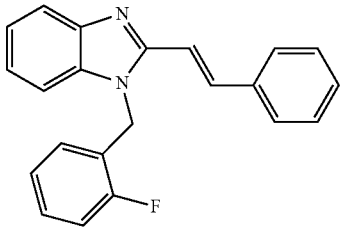 [SMILES: Fc1ccccc1Cn1c(/C=C/c2ccccc2)nc2ccccc21] | >10 | >15 |
| CAP01548 | 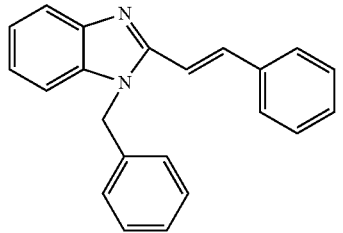 [SMILES: C(=C\c1nc2ccccc2n1Cc1ccccc1)/c1ccccc1] | >15 | >20 |
| CAP01549 | 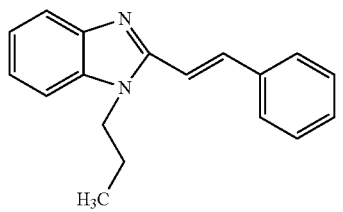 | >20 | >25 |
| CAP01550 | 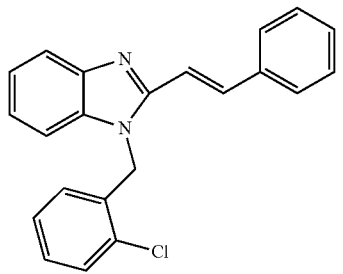 [SMILES: Clc1ccccc1Cn1c(/C=C/c2ccccc2)nc2ccccc21] | 0.74 | 2.40 |

TABLE 2-continued

| ID | Structure | FKBP12 Ki (μM) or % | FKBP52 Ki (μM) or % |
|---|---|---|---|
| CAP01551 | benzimidazole with N-(4-methylbenzyl) and 2-(4-fluorostyryl) | 0.36 | 1.68 |
| CAP01552 | benzimidazole with N-benzyl and 2-(4-chlorostyryl) | 0.49 | 1.91 |
| CAP01553 | benzimidazole with N-propargyl and 2-styryl | 15% at 20 μM | 30% at 20 μM |
| CAP01554 | benzimidazole with N-butyl and 2-styryl | >10 | >15 |
| CAP01555 | benzimidazole with N-isobutyl and 2-styryl | >15 | >20 |
| CAP01557 | benzimidazole with N-butyl and 2-(4-fluorostyryl) | 1.80 | 8.24 |

TABLE 2-continued

| ID | Structure | FKBP12 Ki (μM) or % | FKBP52 Ki (μM) or % |
|---|---|---|---|
| CAP01558 | 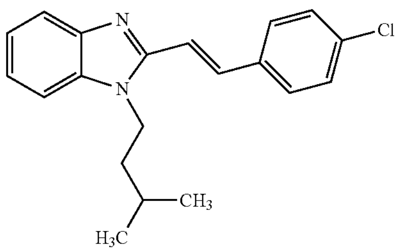 | 0.66 | 4.27 |
| CAP01559 | 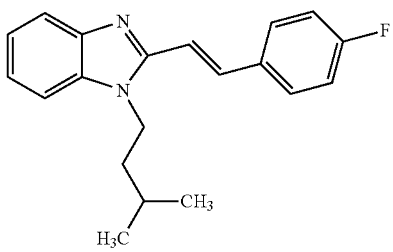 [SMILES: CCCCn1c(/C=C/c2ccc(F)cc2)nc2ccccc21] | 1.08 | 3.03 |
| CAP01560 | 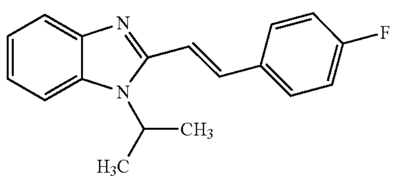 [SMILES: CC(C)n1c(/C=C/c2ccc(F)cc2)nc2ccccc21] | 43% at 20 μM | 35% at μM |
| CAP01562 | 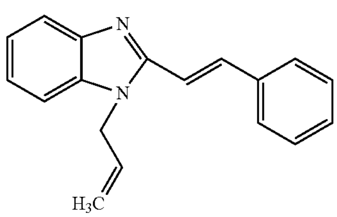 [SMILES: C=CCn1c(/C=C/c2ccccc2)nc2ccccc21] | 0.56 | 25.30 |
| SKD- | 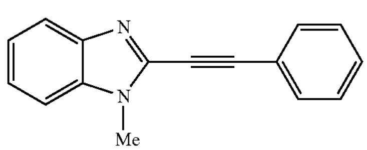 [SMILES: Cn1c(C#Cc2ccccc2)nc2ccccc21] | ND | ND |
| SKD-II-35 | 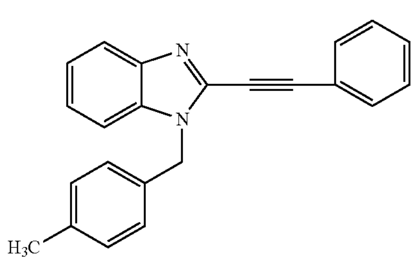 [SMILES: Cc1ccc(Cn2c(C#Cc3ccccc3)nc3ccccc32)cc1] | ND | ND |

TABLE 3

Benzimidazole-diazenylphenyl series FKBP inhibitors

| ID | Structure | FKBP12 Ki (μM) or % | FKBP52 Ki (μM) or % |
|---|---|---|---|
| CAP01194 | 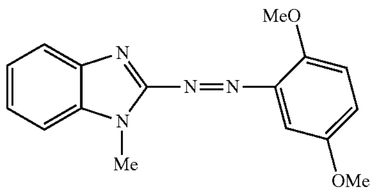 [SMILES: COc1ccc(OC)c(N=Nc2nc3ccccc3n2C)c1] | ND | ND |
| CAP01314 | 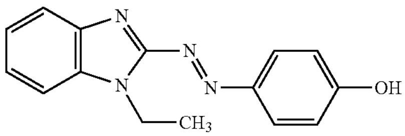 [SMILES: CCn1c(/N=N/c2ccc(O)cc2)nc2ccccc21] | ND | ND |
| CAP01311 | 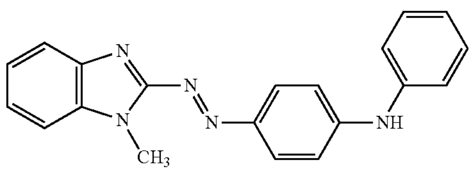 [SMILES: Cn1c(/N=N/c2ccc(Nc3ccccc3)cc2)nc2ccccc21] | ND | ND |
| CAP01310 | 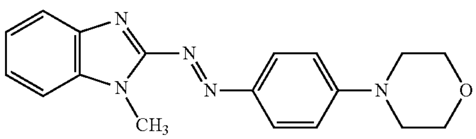 [SMILES: Cn1c(/N=N/c2ccc(N3CCOCC3)cc2)nc2ccccc21] | ND | ND |
| CAP01309 | 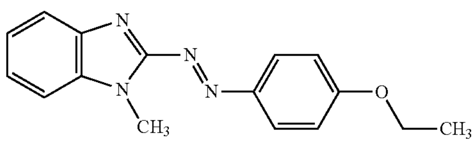 [SMILES: CCOc1ccc(/N=N/c2nc3ccccc3n2C)cc1] | ND | ND |
| CAP01318 | 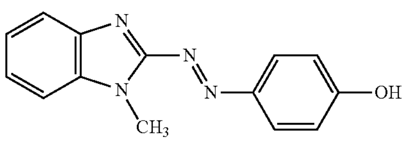 [SMILES: Cn1c(/N=N/c2ccc(O)cc2)nc2ccccc21] | 1.15 | 0.09 |
| CAP01317 | 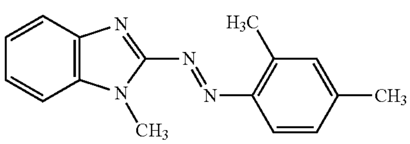 [SMILES: Cc1ccc(/N=N/c2nc3ccccc3n2C)c(C)c1] | ND | ND |
| CAP01316 | 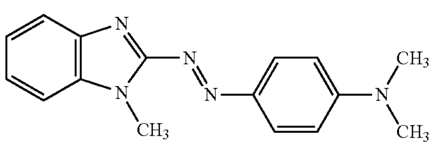 [SMILES: CN(C)c1ccc(/N=N/c2nc3ccccc3n2C)cc1] | 0.77 | 0.2 |
| CAP01329 | 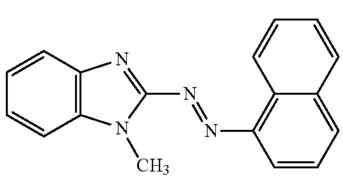 [SMILES: Cn1c(/N=N/c2cccc3ccccc23)nc2ccccc21] | 2.06 | 1.22 |

TABLE 3-continued
Benzimidazole-diazenylphenyl series FKBP inhibitors
| ID | Structure | FKBP12 Ki (μM) or % | FKBP52 Ki (μM) or % |
|---|---|---|---|
| CAP01328 | 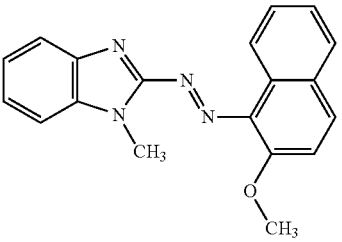 [SMILES: COc1ccc2ccccc2c1/N=N/c1nc2ccccc2n1C] | 0.20 | 0.31 |
| CAP01327 | 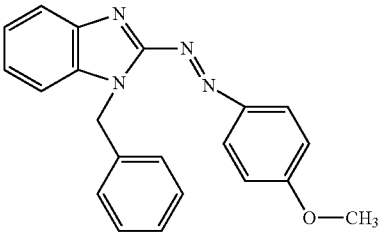 [SMILES: COc1ccc(/N=N/c2nc3ccccc3n2Cc2ccccc2)cc1] | ND | ND |
| CAP01326 | 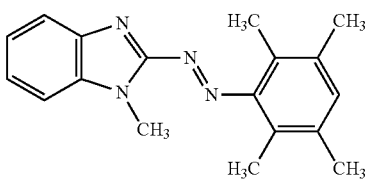 [SMILES: Cc1cc(C)c(C)c(/N=N/c2nc3ccccc3n2C)c1C] | ND | ND |
| CAP01325 | 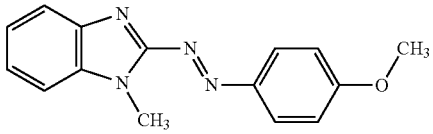 | ND | ND |
| CAP01324 | 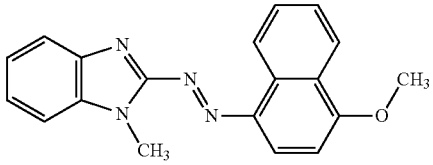 [SMILES: COc1ccc(/N=N/c2nc3ccccc3n2C)c2ccccc12] | 0.065 | 0.016 |
|  | 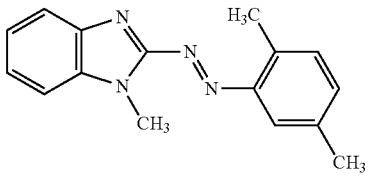 [SMILES: Cc1ccc(C)c(/N=N/c2nc3ccccc3n2C)c1] | ND | ND |
| CAP01333 | 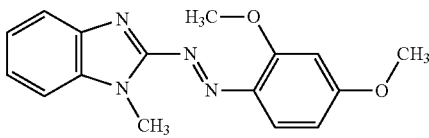 | ND | ND |

TABLE 3-continued

Benzimidazole-diazenylphenyl series FKBP inhibitors

| ID | Structure | FKBP12 Ki (μM) or % | FKBP52 Ki (μM) or % |
|---|---|---|---|
| CAP01332 | 1-methyl-benzimidazol-2-yl-azo-naphthalenyl with HN-phenyl substituent | 0.17 | |
| CAP01358 | 1-methyl-benzimidazol-2-yl-azo-naphthalenyl with OH substituent | 0.24 | 1.10 |
| CAP01359 | 1-methyl-benzimidazol-2-yl-azo-(2,5-dimethoxyphenyl) | ND | ND |

Example 21: Neuroprotection

BE(2)-M17 human neuroblastoma cells engineered to stably express either wild type or A53T mutant α-synuclein, PC12 rat pheochromocytoma cells, or SH-SY5Y human neuroblastoma cells were cultured in 96-well cell culture dishes in a humidified incubator at 37° C. and 5% $CO_2$. The growth medium was supplemented with 0.1% dimethyl sulfoxide (vehicle control) or compounds dissolved in dimethyl sulfoxide. Following 2 hours of exposure to compounds, the growth medium was further supplemented with 6-hydroxydopamine (OHDA) or 0.1% ascorbic acid vehicle control) and incubated for an additional 24-48 hours.

Figure 4A:
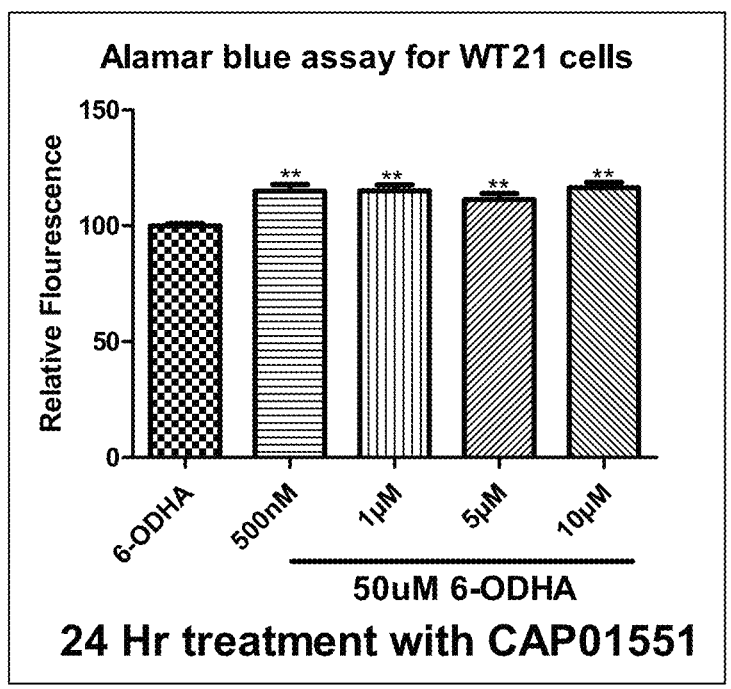
FIG. 4A is a bar graph showing neuroprotection in wild type α-synuclein overexpressing cells (WT21) resulting from treating the cells with dual acting FKBP12 and FKBP52 inhibitory exemplary compound CAP01551, as measured by Alamar Blue assay.
Figure 4B:
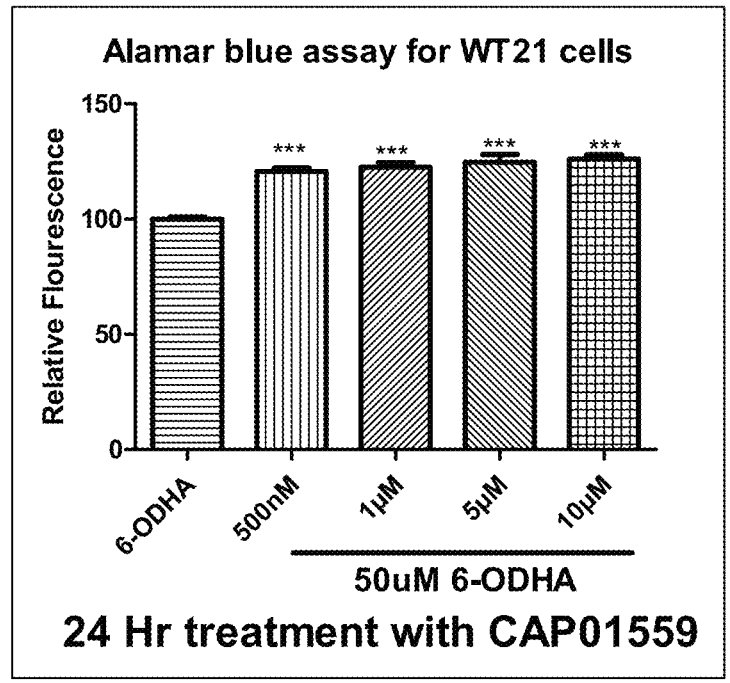
FIG. 4B is a bar graph showing neuroprotection in WT21 cells resulting from treating the cells with dual acting FKBP12 and FKBP52 inhibitory exemplary compound CAP01559, as measured by Alamar Blue assay.
Figure 5:
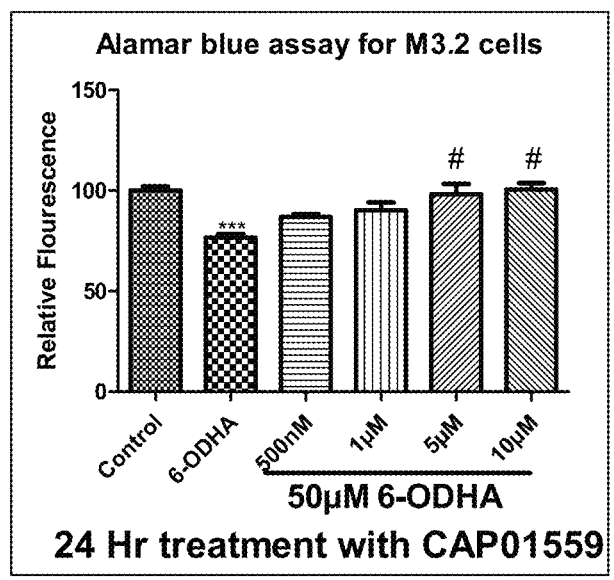
FIG. 5 is a bar graph showing neuroprotection in A53T mutant α-synuclein overexpressing BE(2)-M17 cells (M3.2) resulting from treating the cells with dual acting FKBP12 and FKBP52 inhibitory exemplary compound CAP01559, as measured by Alamar Blue assay.

Cell viability was measured by reduction of WST-8 or alamarBlue® and the relative protection from 6-hydroxydopamine was measured by calculating the percentage of viable cells normalized to 6-hydroxydopamine treated cells in the absence of compound. See FIGS. 4A and 4B for neuroprotection obtained by treating wild type α-synuclein overexpressing cells (WT21) cells with dual acting FKBP12 and FKBP52 inhibitory exemplary compounds CAP01551 (FIG. 4A) and CAP01559 (FIG. 4B). Neuroprotection can be seen also in FIG. 5, which shows results of treating A53T mutant α-synuclein overexpressing cells (M3.2) with CAP01559.

Example 22: Neurite Outgrowth

Figure 6A:
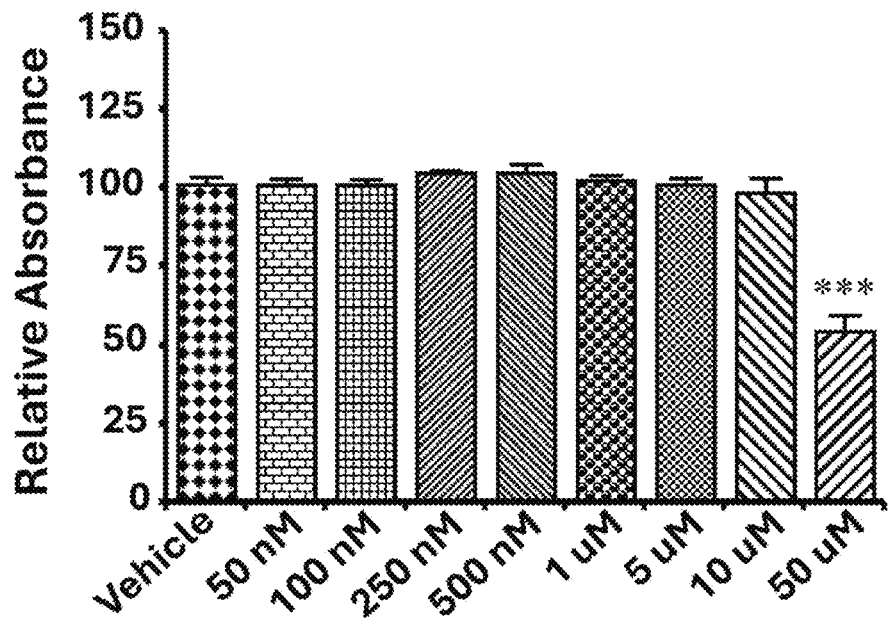
FIG. 6A is a bar graph showing that the exemplary compound CAP01324 is not cytotoxic to WT21 cells at concentrations under 50 µM, as determined by the observed relative change in absorbance upon reduction of MTS tetrazolium dye.
Figure 6B:
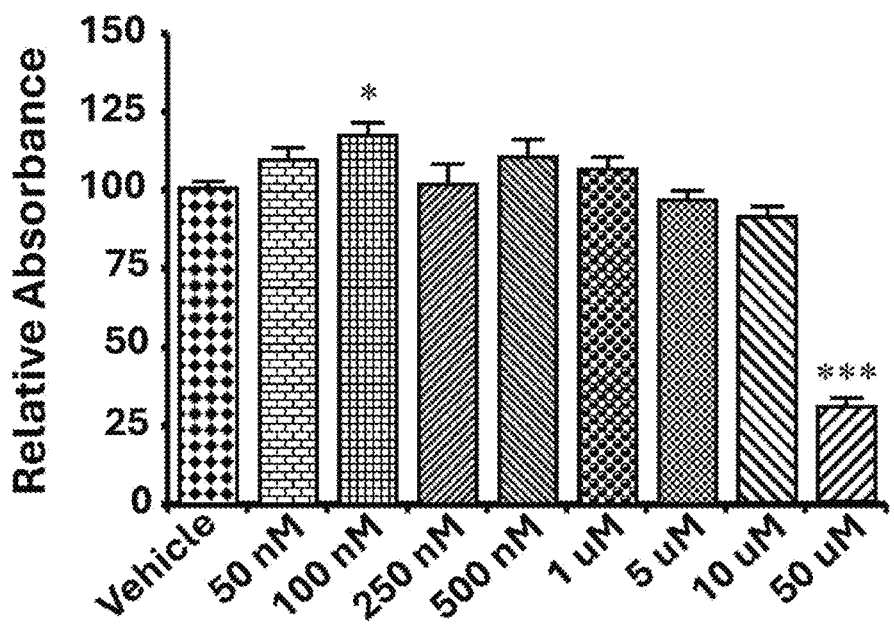
FIG. 6B is a bar graph showing neuroprotection in A53T mutant cells conferred by CAP01324 (100 nM) as determined by the observed relative change in absorbance upon reduction of MTS tetrazolium dye.
Figure 6C:
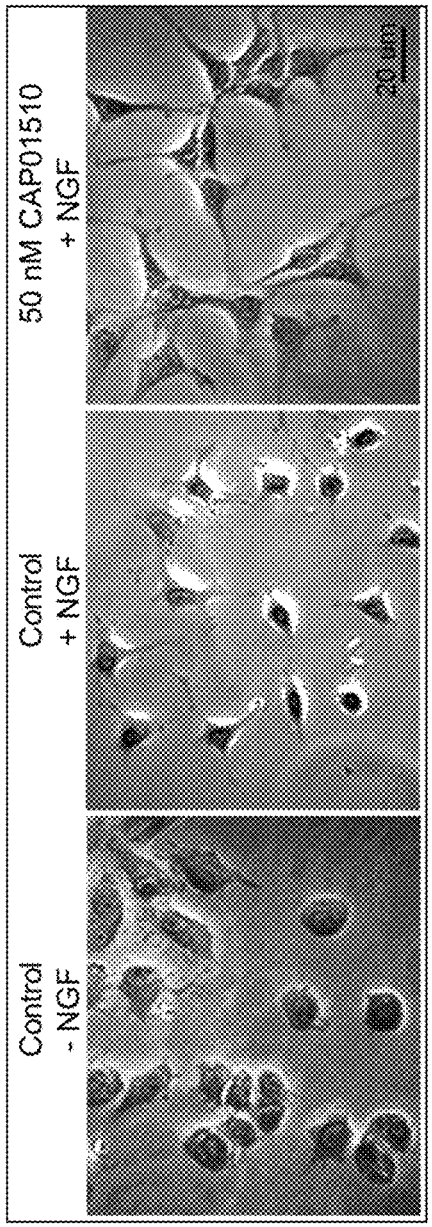
FIG. 6C shows light microscopy images of neurite outgrowth of PC12 cells treated with control (DMSO) and FKBP12 and FKBP52 inhibitory exemplary compound CAP01510.
Figure 6D:
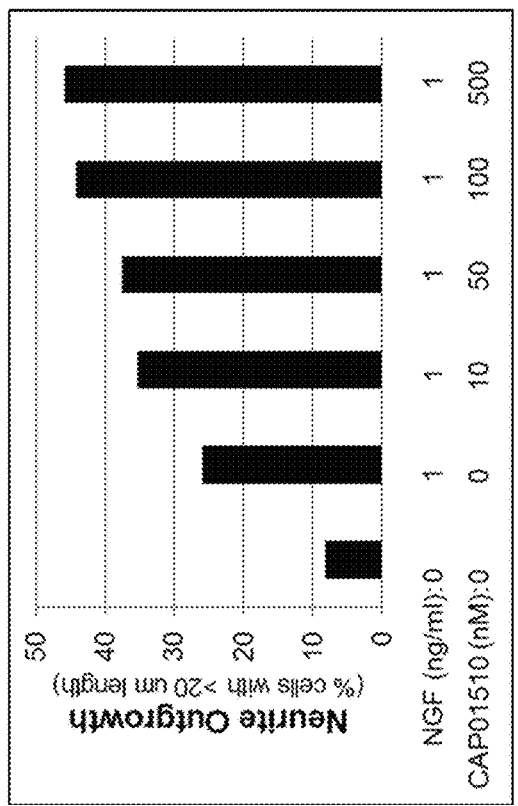
FIG. 6D is a bar graph showing dose dependent promotion of neurite outgrowth by dual acting FKBP12 and FKBP52 inhibitory exemplary CAP01510.

PC12 rat pheochromocytoma or SH-SY5Y human neuroblastoma cells were grown on glass coverslips in a 24-well cell culture dish in a humidified incubator at 37° C. and 5% $CO_2$. After 24 hours, the cells were washed with phosphate buffered saline and the serum concentration of the growth medium was reduced to 0.2%. After 16 hours in the reduced serum medium, 0.1% dimethyl sulfoxide (vehicle control), or compounds dissolved in dimethyl sulfoxide were added to the growth medium. Following 2 hours of exposure to the compounds, the growth medium was supplemented with 6-hydroxydopamine (OHDA) or 0.1% ascorbic acid vehicle control, nerve growth factor (or phosphate-buffered saline vehicle control), in addition to 0.1% dimethyl sulfoxide (vehicle control) or compounds dissolved in dimethyl sulfoxide. After 24 hours incubation the medium was removed and replaced with ice-cold methanol and cells were incubated for 10 minutes at −20° C. The cells were washed twice with phosphate-buffered saline and mounted on slides for light microscopy. Phase contrast images were captured at 20× magnification and the percentage of cells with neurites longer than 20 μm were scored for approximately 200 cells in each condition using ImageJ software. See FIGS. 6C and 6D for promotion of neurite outgrowth by dual acting FKBP12 and FKBP52 inhibitory exemplary compound CAP01510.

Example 23: Distribution of Inhibitors in Plasma and Brain

Distribution of inhibitors in plasma and brain tissue was examined after intravenous dosing of mice with inhibitors. The experimental conditions were as follows: Mice: male CD1 about 8 weeks old; body weight: about 25 g; No. of groups: one; No. of animals per group: 5; vehicle for IV dosing: DMSO; dosage: 1 mg/kg. Samples were collected at the time points shown in Table 4 below.

TABLE 4

| | Time, h | | |
|---|---|---|---|
| | 0.15 | 0.5 | 1 |
| Sample collected | Plasma | Plasma | Plasma and Brain |
| Number of Plasma sample | 2 | 2 | 2 |
| Number of Brain sample | 0 | 0 | 2 |

Plasma samples were separated by centrifugation in presence of K2-EDTA as anticoagulant. Brain tissue were homogenized in phosphate buffer saline and processed for bioanalysis as per standard practice. Samples were analyzed by a discovery grade bio-analytical method using LC-MS/MS method. Results obtained are shown below.

TABLE 5

Mice PK/TD data summary from 1 mg/Kg, i.v. dose

| Time (h) | CAP01551 | CAP01723 |
|---|---|---|
| 0.15 | 194.6 ± 69.9 | 239.7 ± 14.2 |
| 0.5 | 65.4 ± 16.2 | 100.5 ± 5.1 |
| 1.0 | 33.8 ± 11.0 | 49.8 ± 6.8 |

Note:
results are expressed in mean ± SD, n = 5 animals/time/point; discrete method sampling Post 1 h blood sampling, animals were decapitated and brain samples collected for LC-MS analysis.

TABLE 6

Mice PK/TD study data summary of CAP01551 from 1 mg/kg, IV dose

| Time (h) | A#1 | A#2 | A#3 | A#4 | A#5 | Mean | SD |
|---|---|---|---|---|---|---|---|
| Plasma Concentrations (ng/mL) | | | | | | | |
| 0.15 | 217.36 | 295.33 | 122.46 | 203.22 | 134.60 | 194.59 | 69.90 |
| 0.5 | 71.90 | 88.98 | 46.31 | 62.88 | 56.74 | 65.36 | 16.16 |
| 1 | 33.70 | 52.86 | 27.45 | 27.24 | 27.74 | 33.80 | 10.99 |
| Results Plasma concentrations (ng/mL) | | | | | | | |
| 1 h | 33.70 | 52.86 | 27.45 | 27.24 | 27.74 | 33.80 | 10.99 |
| Brain concentrations (ng/G) | | | | | | | |
| 1 h | 73.77 | 81.88 | 57.91 | 63.84 | 74.50 | 70.38 | 9.47 |
| Brain/Plasma ratio: | | | | 2.1 | | | |

Mice PK/TD study data summary of CAP01723 from 1 mg/kg, IV dose

| Time (h) | Mice #6 | Mice #7 | Mice #8 | Mice #9 | Mice #10 | Mean | SD |
|---|---|---|---|---|---|---|---|
| Plasma Concentrations (ng/mL) | | | | | | | |
| 0.15 | 245.6 | 258.2 | 225.3 | 225.4 | 244.2 | 239.7 | 14.2 |
| 0.5 | 103.1 | 106.1 | 97.6 | 102.6 | 93.2 | 100.5 | 5.1 |
| 1 | 50.3 | 41.1 | 58.7 | 53.5 | 45.4 | 49.8 | 6.8 |
| Plasma concentrations (ng/mL) | | | | | | | |
| 1 h | 50.3 | 41.1 | 58.7 | 53.5 | 45.4 | 49.8 | 6.8 |
| Brain concentrations (ng/G) | | | | | | | |
| 1 h | 17.2 | 14.6 | 31.9 | 9.5 | 22.3 | 19.1 | 8.5 |
| B/P ratio | | | | 0.38 | | | |

Example 24: Microsomal Stability Analysis

Microsomal stability measurements were carried out by Clint assay. Test compounds were incubated with liver microsome, and metabolic stability was determined over 45 minutes. The experimental conditions were as follows. Compound concentration: 1 µM; assay conditions: 100 mM potassium phosphate buffer pH 7.4 with 1 mM NADPH; Time of incubation: 0, 5, 10, 15, 30 and 45 minutes at 37° C.; species: rat (Male SD) and human (pooled Mixed gender); protein concentration in assay: 0.5 mg/mL; analysis: LC-MS/MS; QC compound: verapamil (high clearance), atenolol (low clearance); and results: Clint (µL/min/mg protein), half-life (min). Results of the measurement are shown below in Table 7.

TABLE 7

Microsomal Stability Analysis

| ID | Human microsomes $T_{1/2}$ (min) | Clearance CL int (µL/min/mg protein) | Rat microsomes $T_{1/2}$ (min) | Clearance CL int (µL/min/mg protein) |
|---|---|---|---|---|
| CAP01551 | 26.45 | 52.39 | 6.85 | 202.21 |
| CAP01723 | 8.29 | 167.14 | 10.69 | 129.65 |
| Verapamil Positive control (FDA approved Drug) | 8.55 | 162.13 | 6.66 | 208.02 |

REFERENCES

Bollini S, Herbst J J, Gaughan G T, Verdoorn T A, Ditta J, Dubowchik G M, Vinitsky A. (2002) J Biomol Screen. December; 7(6):526-30.

Deleersnijder A, Van Rompuy A S, Desender L, Pottel H, Buée L, Debyser Z, Baekelandt V, Gerard M. (2011). J Biol Chem. 286(30):26687-26701.

Gerard M, Debyser Z, Desender L, Kahle P J, Baert J, Baekelandt V, Engelborghs Y (2006) The aggregation of alpha-synuclein is stimulated by FK506 binding proteins as shown by fluorescence correlation spectroscopy. FASEB J 20:524-526

Gerard M, Debyser Z, Desender L, Baert J, Brandt I, Baekelandt V, Engelborghs Y (2008) FK506 binding protein 12 differentially accelerates fibril formation of wild type alpha-synuclein and its clinical mutants A30P or A53T. J Neurochem 106:121-133.

Gerard M, Deleersnijder A, Daniëls V, Schreurs S, Munck S, Reumers V, Pottel H, Engelborghs Y, Van den Haute C, Taymans J M, Debyser Z, Baekelandt V. (2010). J Neurosci., 30(7):2454-2463.

Gerard M, Deleersnijder A, Demeulemeester J, Debyser Z, Baekelandt V. (2011). Mol Neurobiol. 44(1):13-27.

Göthel S F, Marahiel M A (1999) Peptidyl-prolyl cis-trans isomerases, a superfamily of ubiquitous folding catalysts. Cell Mol Life Sci 55:423-436

Galat A (2003) Peptidylprolyl cis/trans isomerases (immunophilins): biological diversity-targets-functions. Curr Top Med Chem 3:1315-1347

Nikolovska-Coleska Z, Wang R, Fang X, Pan H, Tomita Y, Li P, Roller P P, Krajewski K, Saito N G, Stuckey J A, Wang S. (2004) Anal Biochem. September 15; 332(2): 261-73.

Rulten S L, Kinloch R A, Tateossian H, Robinson C, Gettins L, Kay J E (2006) The human FK506-binding proteins: characterization of human FKBP19. Mamm Genome 17:322-331.

Souvik Chattopadhaya, Amaravadhi Harikishore and Ho Sup Yoon (2012). Role of FKBPs in Parkinson's Disease, Mechanisms in Parkinson's Disease—Models and Treatments, Dr. Juliana Dushanova (Ed.), ISBN: 978-953-307-876-2, InTech, DOI: 10.5772/22419. Available from: http://www.intechopen.com/books/mechanisms-in-parkinson-s-disease-models-and-treatments/role-of-fkbps-in-parkinson-s-disease.

Charters A R, Kobayashi M, Butcher S P (1994a) Immunochemical analysis of FK506 binding proteins in neuronal cell lines and rat brain. Biochem Soc Trans 22:411S Charters A R, Kobayashi M, Butcher S P (1994b) The subcellular distribution of FK506 binding proteins in rat brain. Biochem Soc Trans 22:412S Steiner J P, Dawson T M, Fotuhi M, Glatt C E, Snowman A M, Cohen N, Snyder S H (1992) High brain densities of the immunophilin FKBP colocalized with calcineurin. Nature 358:584-587

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical composition comprising a compound or a pharmaceutically acceptable salt thereof, and a pharmaceutically acceptable carrier, wherein the compound is of Formula (II):

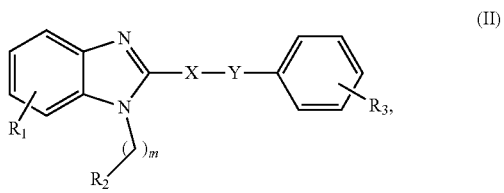

wherein $R_1$ is selected from hydrogen; halogen; nitro; cyano; amino; hydroxy; carboxy; $(C_1\text{-}C_6)$alky; halo $(C_1\text{-}C_6)$alkyl; $(C_1\text{-}C_6)$alkoxy; halo$(C_1\text{-}C_6)$alkoxy; $(C_3\text{-}C_{10})$cycloalkyl; halo$(C_3\text{-}C_{10})$cycloalkyl; $(C_3\text{-}C_{10})$cycloalkylthio; halo$(C_3\text{-}C_{10})$cycloalkythio; $(C_3\text{-}C_{10})$heterocycloalkyl; halo$(C_3\text{-}C_{10})$heterocycloalky; $(C_1\text{-}C_6)$alkylamino; di$(C_1\text{-}C_6)$alkylamino; $(C_1\text{-}C_6)$alkylthio; halo$(C_1\text{-}C_6)$alkylthio; $(C_1\text{-}C_6)$alkylsulfinyl; halo$(C_1\text{-}C_6)$alkylsulfinyl; $(C_1\text{-}C_6)$alkylsulfonyl; halo$(C_1\text{-}C_6)$alkylsulfonyl; $(C_3\text{-}C_{10})$cycloalkylsulfinyl; halo$(C_3\text{-}C_{10})$cycloalkylsulfinyl; $(C_3\text{-}C_{10})$cycloalkylsulfonyl; halo$(C_3\text{-}C_{10})$cycloalkylsulfonyl; aryl, heteroaryl, arylamine, or heterocyclyl, optionally substituted with halogen, nitro, cyano, amino, hydroxy, carboxy, $(C_1\text{-}C_6)$alkyl, halo$(C_1\text{-}C_6)$alkyl, $(C_1\text{-}C_6)$alkoxy, or halo$(C_1\text{-}C_6)$alkoxy; and an aryl ring fused to the relevant phenyl ring, either ring being optionally substituted with halogen, nitro, cyano, amino, hydroxy, carboxy, $(C_1\text{-}C_6)$alkyl, halo$(C_1\text{-}C_6)$alkyl, $(C_1\text{-}C_6)$alkoxy, halo$(C_1\text{-}C_6)$alkoxy or arylamine;

$R_3$ is selected from halogen; nitro; cyano; amino; hydroxy; carboxy; $(C_1\text{-}C_6)$alkyl; halo$(C_1\text{-}C_6)$alkyl; $(C_1\text{-}C_6)$alkoxy; halo$(C_1\text{-}C_6)$alkoxy; $(C_3\text{-}C_{10})$cycloalkyl; halo$(C_3\text{-}C_{10})$cycloalkyl; $(C_3\text{-}C_{10})$cycloalkylthio; halo$(C_3\text{-}C_{10})$cycloalkylthio; $(C_3\text{-}C_{10})$heterocycloalkyl; halo$(C_3\text{-}C_{10})$heterocycloalkyl; $(C_1\text{-}C_6)$alkylamino; di$(C_1\text{-}C_6)$alkylamino; $(C_1\text{-}C_6)$alkylthio; halo$(C_1\text{-}C_6)$alkylthio; $(C_1\text{-}C_6)$alkylsulfinyl; halo$(C_1\text{-}C_6)$alkylsulfinyl; $(C_1\text{-}C_6)$alkylsulfonyl; halo$(C_1\text{-}C_6)$alkylsulfonyl; $(C_3\text{-}C_{10})$cycloalkylsulfinyl; halo$(C_3\text{-}C_{10})$cycloalkylsulfinyl; $(C_3\text{-}C_{10})$cycloalkylsulfonyl; halo$(C_3\text{-}C_{10})$cycloalkylsulfonyl; aryl, heteroaryl, arylamine, or heterocyclyl, optionally substituted with halogen, nitro, cyano, amino, hydroxy, carboxy, $(C_1\text{-}C_6)$alkyl, halo$(C_1\text{-}C_6)$alkyl, $(C_1\text{-}C_6)$alkoxy, or halo$(C_1\text{-}C_6)$alkoxy; and an aryl ring fused to the relevant phenyl ring, either ring being optionally substituted with halogen, nitro, cyano, amino, hydroxy, carboxy, $(C_1\text{-}C_6)$alkyl, halo$(C_1\text{-}C_6)$alkyl, $(C_1\text{-}C_6)$alkoxy, halo$(C_1\text{-}C_6)$alkoxy or arylamine;

X—Y is CH=CH, C≡C, or N=N;

$R_2$ is selected from $(C_1\text{-}C_6)$alkyl; halo$(C_1\text{-}C_6)$alkyl; $(C_2\text{-}C_6)$alkenyl; halo$(C_2\text{-}C_6)$alkenyl;

($C_2$-$C_6$)alkynyl; halo($C_2$-$C_6$)alkynyl; ($C_3$-$C_{10}$)cycloalkyl; halo($C_3$-$C_{10}$)cycloalkyl; heterocyclyl, aryl, or heteroaryl, each optionally substituted with one or more groups independently selected from halogen, nitro, cyano, amino, hydroxy, carboxy, ($C_1$-$C_6$)alkyl, halo($C_1$-$C_6$)alkyl, ($C_1$-$C_6$)alkoxy, or halo($C_1$-$C_6$)alkoxy; and m is 0 to 4.

2. A method of alleviating Parkinson's disease in a subject, comprising administering to the subject a therapeutically effective amount of the pharmaceutical composition of claim 1.

3. The pharmaceutical composition of claim 1 for nasal administration, wherein the pharmaceutically acceptable carrier comprises a lipid and a non-ionic surfactant, and wherein the pharmaceutical composition further comprises an effective amount of an absorption promoting agent to allow nasal absorption of a pharmacologically effective amount of the compound.

4. The composition of claim 3, wherein the absorption promoting agent is a cationic polymer.

5. A method of alleviating Parkinson's disease in a subject, comprising administering to the subject a therapeutically effective amount of the pharmaceutical composition of claim 3.

6. The method of claim 5, wherein the absorption promoting agent is a cationic polymer.

7. A compound of Formula (II):

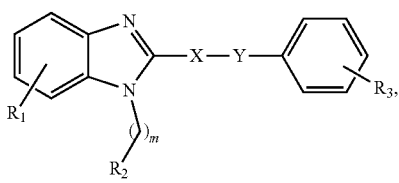

(II)

or a pharmaceutically acceptable salt thereof,
wherein $R_1$ is selected from hydrogen; halogen; nitro; cyano; amino; hydroxy; carboxy; ($C_1$-$C_6$)alky; halo($C_1$-$C_6$)alkyl; ($C_1$-$C_6$)alkoxy; halo($C_1$-$C_6$)alkoxy; ($C_3$-$C_{10}$)cycloalkyl; halo($C_3$-$C_{10}$)cycloalkyl; ($C_3$-$C_{10}$)cycloalkylthio; halo($C_3$-$C_{10}$)cycloalkythio; ($C_3$-$C_{10}$)heterocycloalkyl; halo($C_3$-$C_{10}$)heterocycloalky; ($C_1$-$C_6$)alkylamino; di($C_1$-$C_6$)alkylamino; ($C_1$-$C_6$)alkylthio; halo($C_1$-$C_6$)alkylthio; ($C_1$-$C_6$)alkylsulfinyl; halo($C_1$-$C_6$)alkylsulfinyl; ($C_1$-$C_6$)alkylsulfonyl; halo($C_1$-$C_6$)alkylsulfonyl; ($C_3$-$C_{10}$)cycloalkylsulfinyl; halo($C_3$-$C_{10}$)cycloalkylsulfinyl; ($C_3$-$C_{10}$)cycloalkylsulfonyl; halo($C_3$-$C_{10}$)cycloalkylsulfonyl; aryl, heteroaryl, arylamine, or heterocyclyl, optionally substituted with halogen, nitro, cyano, amino, hydroxy, carboxy, ($C_1$-$C_6$)alkyl, halo($C_1$-$C_6$)alkyl, ($C_1$-$C_6$)alkoxy, or halo($C_1$-$C_6$)alkoxy; and an aryl ring fused to the relevant phenyl ring, either ring being optionally substituted with halogen, nitro, cyano, amino, hydroxy, carboxy, ($C_1$-$C_6$)alkyl, halo($C_1$-$C_6$)alkyl, ($C_1$-$C_6$)alkoxy, halo($C_1$-$C_6$)alkoxy or arylamine;

$R_3$ is selected from halogen; nitro; cyano; amino; hydroxy; carboxy; ($C_1$-$C_6$)alkyl; halo($C_1$-$C_6$)alkyl; ($C_1$-$C_6$)alkoxy; halo($C_1$-$C_6$)alkoxy; ($C_3$-$C_{10}$)cycloalkyl; halo($C_3$-$C_{10}$)cycloalkyl; ($C_3$-$C_{10}$)cycloalkylthio; halo($C_3$-$C_{10}$)cycloalkylthio; ($C_3$-$C_{10}$)heterocycloalkyl; halo($C_3$-$C_{10}$)heterocycloalkyl; ($C_1$-$C_6$)alkylamino; di($C_1$-$C_6$)alkylamino; ($C_1$-$C_6$)alkylthio; halo($C_1$-$C_6$)alkylthio; ($C_1$-$C_6$)alkylsulfinyl; halo($C_1$-$C_6$)alkylsulfinyl; ($C_1$-$C_6$)alkylsulfonyl; halo($C_1$-$C_6$)alkylsulfonyl; ($C_3$-$C_{10}$)cycloalkylsulfinyl; halo($C_3$-$C_{10}$)cycloalkylsulfinyl; ($C_3$-$C_{10}$)cycloalkylsulfonyl; halo($C_3$-$C_{10}$)cycloalkylsulfonyl; aryl, heteroaryl, arylamine, or heterocyclyl, optionally substituted with halogen, nitro, cyano, amino, hydroxy, carboxy, ($C_1$-$C_6$)alkyl, halo($C_1$-$C_6$)alkyl, ($C_1$-$C_6$)alkoxy, or halo($C_1$-$C_6$)alkoxy; and an aryl ring fused to the relevant phenyl ring, either ring being optionally substituted with halogen, nitro, cyano, amino, hydroxy, carboxy, ($C_1$-$C_6$)alkyl, halo($C_1$-$C_6$)alkyl, ($C_1$-$C_6$)alkoxy, halo($C_1$-$C_6$)alkoxy or arylamine;

X—Y is C≡C;
$R_2$ is a ($C_2$-$C_6$)alkenyl or a ($C_2$-$C_6$)alkynyl; and
m is 1.

8. The compound of claim 7, wherein $R_1$ is hydrogen.

9. A compound having formula:

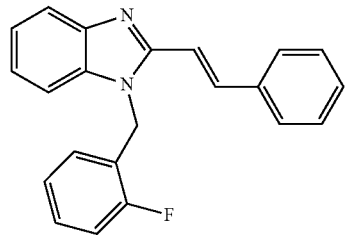 [SMILES: Fc1ccccc1Cn1c(/C=C/c2ccccc2)nc2ccccc21]

or a pharmaceutically acceptable salt thereof.

* * * * *